United States Patent
Verheijden et al.

(10) Patent No.: US 11,274,159 B2
(45) Date of Patent: Mar. 15, 2022

(54) ANTI-SIRPα ANTIBODIES

(71) Applicant: Byondis B.V., Nijmegen (NL)

(72) Inventors: Gijsbertus Franciscus Maria Verheijden, Nijmegen (NL); Gerard Rouwendal, Nijmegen (NL); Roland Jan Arends, Nijmegen (NL); Timo Kars Van Den Berg, Amsterdam (NL); Hanke Lottie Matlung, Amsterdam (NL); Katarina Franke, Amsterdam (NL)

(73) Assignee: Byondis B.V., Nijmegen (NL)

( * ) Notice: Subject to any disclaimer, the term of this patent is extended or adjusted under 35 U.S.C. 154(b) by 180 days.

(21) Appl. No.: 16/614,199

(22) PCT Filed: May 15, 2018

(86) PCT No.: PCT/EP2018/062473
§ 371 (c)(1),
(2) Date: Nov. 15, 2019

(87) PCT Pub. No.: WO2018/210793
PCT Pub. Date: Nov. 22, 2018

(65) Prior Publication Data
US 2021/0070874 A1    Mar. 11, 2021

(30) Foreign Application Priority Data

May 16, 2017  (EP) ..................... 17171285

(51) Int. Cl.
*C07K 16/28* (2006.01)
*A61K 45/06* (2006.01)
(52) U.S. Cl.
CPC .......... *C07K 16/2896* (2013.01); *A61K 45/06* (2013.01); *C07K 2317/24* (2013.01); *C07K 2317/565* (2013.01); *C07K 2317/72* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 2003/0054415 A1 | 3/2003 | Buhring et al. |
| 2015/0166654 A1 | 6/2015 | Igawa et al. |
| 2016/0340397 A1 | 11/2016 | Ring |

FOREIGN PATENT DOCUMENTS

| WO | 2013056352 A1 | 4/2013 |
| WO | 2013150043 A1 | 10/2013 |
| WO | 2014127906 A1 | 8/2014 |
| WO | 2015138600 A2 | 9/2015 |
| WO | 2017068164 A1 | 4/2017 |
| WO | 2017178653 A2 | 10/2017 |
| WO | 2018026600 A1 | 2/2018 |

OTHER PUBLICATIONS

Written Opinion of the International Searching Authority of PCT/EP2018/062473; dated Nov. 22, 2018. (Year: 2018).*
Zhao et al., "CD-47 signal regulatory protein-α (SIRPα) interactions form a barrier for antibody-mediated tumor cell destruction," PNAS, vol. 108, No. 45, Nov. 8, 2011, pp. 18342-18347.
E.M. Van Beek et al., "Signal Regulatory Proteins in the Immune System," The Journal of Immunology, vol. 175, No. 12, Dec. 8, 2005, pp. 7781-7787.
Matozaki et al., "Functions and molecular mechanisms of the CD47-SIRPalpha signalling pathway," Trends in Cell Biology, Elsevier Science Ltd., vol. 19, No. 2, Feb. 2003, pp. 72-80.
Hayashi et al., "Positive Regulation of Phagocytosis by SIRPβ and its Signaling Mechanism in Macrophages," Journal of Biological Chemistry, vol. 279, No. 28, Jul. 9, 2004, pp. 29450-29460.
P. A. Oldenborg, "Role of CD47 as a Marker of Self on Red Blood Cells," Science, vol. 288, No. 5473, Jun. 16, 2000, pp. 2051-2054.
Jiang et al., "Integrin-Associated Protein is a Ligand for the P84 Neural Adhesion Molecule," Journal of Biological Chemistry, American Society for Biochemistry and Molecular Biology, US, vol. 274, No. 2, Jan. 8, 1999, pp. 559-562.
Chuang et al., "Central Nervous System Antigen P84 Can Serve as a Substrate for Neurite Outgrowth," Developmental Biology, Elsevier, Amsterdam, NL, vol. 137, No. 2, Feb. 1, 1990, pp. 219-232.
Liu et al., "Signal Regulatory Protein (SIRPα), a Cellular Ligand for CD47, Regulates Neutrophil Transmigration," Journal of Biological Chemistry, vol. 277, No. 12, Mar. 22, 2002, pp. 10028-10036.
Motegi st al., "Role of the CD47-SHPS-1 system in regulation of cell migration," EMBO (European Molecular Biology Organization) Journal, Wiley, DE, vol. 22, No. 11, 2003 pp. 2634-2644.

(Continued)

*Primary Examiner* — Phillip Gambel
(74) *Attorney, Agent, or Firm* — Buscher Patent PLLC

(57) ABSTRACT

The present invention relates to antibodies against SIRPα that are suitable for use in anti-cancer therapy. The invention further relates to the use of the anti-SIRPα antibodies in the treatment of human solid tumours and haematological malignancies, optionally in combination with other anti-cancer therapeutics. The anti-SIRPalpha antibodies described are more specific than known anti-SIRPalpha antibodies, whereas they show excellent affinity for both SIRPalpha1 and SIRPalphaBIT. In one embodiment the anti-SIRPalpha antibodies do not bind to SIRPgamma. In a second embodiment, the anti-SIRPalpha antibodies do not bind to SIRPgamma and do not bind to SIRPbeta1v1. In a third embodiment, the anti-SIRPalpha antibodies do not bind to SIRPgamma and do not bind to SIRPetav2. In a fourth embodiment, the anti-SIRPalpha antibodies do not bind to SIRPbeta1v1.

10 Claims, 4 Drawing Sheets
Specification includes a Sequence Listing.

(56) References Cited

OTHER PUBLICATIONS

Weiskopf et al., "Direct SIRPα Blockade Augments Macrophage Responses to Therapeutic Anticancer Antibodies," Blood Journal, vol. 124, No. 21, 2014, p. 2729.
Ho et al., "Targeting SIRPα in cancer," OncoImmunology, Landes Bioscience, US, vol. 2, No. 2, Feb. 2013, pp. e23081-e23082.
Zhao et al., "CD47-signal regulatory protein-alpha (SIRPα) interactions form a barrier for antibody-mediated tumor cell destruction: Supporting Information," Proceedings of the National Academy of Sciences, Oct. 31, 2011, pp. 1-3.
Hatherley et al., "The Structure of the Macrophage Signal Regulatory Protein α (SIRPα) Inhibitory Receptor Reveals a Binding Face Reminiscent of That Used by T Cell Receptors," Journal of Biological Chemistry, vol. 282, No. 19, May 11, 2007, pp. 14567-14575.
Nettleship et al., "Crystal structure of signal regulatory protein gamma (SIRP gamma) in complex with an antibody Fab fragment," BMC Structural Biology, Biomed Central Ltd., London, GB, vol. 13, No. 1, Jul. 4, 2013, p. 3.
Liu et al., "Functional Elements on SIRPα IgV Domain Mediate Cell Surface Binding to CD47," Journal of Molecular Biology, Academic Press, United Kingdom, vol. 365, No. 3, Jan. 19, 2007, pp. 680-693.
Lee et al., "Novel Structural Determinants on SIRPα that Mediate Binding to CD47," The Journal of Immunology, 2007, vol. 179, pp. 7741-7750.
Richards et al., "Optimization of antibody binding to Fc gamma RIIa enhances macrophage phagocytosis of tumor cells," Mol. Cancer Ther. Aug. 2008, 7(8), pp. 2517-2527.
Hayes et al., "Fc gamma receptors: glycobiology and therapeutic prospects," J. Inflamm. Res. 2016, 9, pp. 209-219.
Weiskopf, "Cancer immunotherapy targeting the CD47/SIRPα axis," Eur. J. Cancer 2017, 76, pp. 100-109.
Takenaka et al., "Polymorphism in Sirpa modulates engraftment of human hematopoietic stem cells," Nature Immun. Dec. 2007, 8(12), pp. 1313-1323.
Hatherley et al., "Polymorphisms in the Human Inhibitory Signal-regulatory Proten α Do Not Affect Binding to Its Ligand CD47," J. Biol. Chem. vol. 289 No. 14 pp. 10024-10028.
T. van den Berg et al., "Signal Regulatory Proteins in the Immune System," The Journal of Immunology, vol. 175, No. 12, Dec. 8, 2005, pp. 7788-7789.
Piccio et al., "Adhesion of human T cells to antigen-presenting cells through SIRPβ2-CD47 interaction costimulates T-Cell proliferation," Blood, Mar. 15, 2005, vol. 105, No. 6,, pp. 2421-2427.
Stefanidakis et al., "Endothelial CD47 interaaction with SIRP gamma Is required for human T-cell transendothelial migration under shear flow conditions in vitro," Blood, Aug. 15, 2008, vol. 112, No. 4, pp. 1280-1289.
Pleass et al., "Identification of Residues in the CH2/CH3 Domain Interface of IgA Essential for Interaction with the Human Fcα Receptor (FcαR) CD89," J. Biol. Chem. Aug. 13, 1999, vol. 274, No. 33, pp. 23508-23514.
Yanagita et al., "Anti-SIRPα antibodies as a potential new tool for cancer immunotherapy," JCI Insight, 2017, 2(1), e89140.
Köhler et al., "Continuous cultures of fused cells secreting antibody of predefined specificity," Nature, Aug. 7, 1975, vol. 256, pp. 495-497.
Clackson et al., "Making antibody fragments using phage display libraries," Nature, Aug. 15, 1991, vol. 352, pp. 624-628.
Marks et al., "Human Antibodies from V-gene Libraries Displayed on Phage," J Mol. Biol. 1991, 222, pp. 581-597.
Kabat, E.A. et al., Sequences of Proteins of Immunological Interest, 5th Ed. Public Health Service, National Institutes of Health, Bethesda, MD., NIH publication No. 91-3242, pp. 662, 680, 689 (1991).
Chothia et al., "Conformations of immunoglobulin hypervariable regions," Nature, Dec. 28, 1989, vol. 342, No. 21, pp. 877-883.
Lefranc, "The IMGT Unique Numbering for Immunogiobulins, T-Cell Receptors, and Ig-Like Domains," The Immunologist 1999, 7, 132-136.
Soto-Pantoja et al., "CD47 signaling pathways controlling cellular differentiation and responses to stress," Crit. Rev. in Biochem. and Mol. Biol., Feb. 24, 2015, vol. 50, No. 3, pp. 212-230.
E.S. Day et al., "Determining the affinity and stoichiometry of interactions between unmodified proteins in solution using Biacore," Analytical Biochemistry 2013, 440, pp. 96-107.
Harrison et al., "Methods to measure the binding of therapeutic monoclonal antibodies to the human Fc receptor Fc gamma RIII (CD16) using real time kinetic analysis and flow cytometry," J. Pharm. Biomed. Analysis 2012, 63, pp. 23-28.
Vafa et al., "An engineered Fc variant of an IgG eliminates all immune effector functions via structural perturbations," Methods, 2014, 65, pp. 114-126.
Leoh et al., "Insights into the effector functions of human IgG3 in the context of an antibody targeting transferrin receptor 1," Mol. Immunol. Oct. 2015, 67(200), pp. 407-415.
Parekh et al., "Development and validation of an antibody-dependent cell-mediated cytotoxicity-reporter gene assay," mAbs May/Jun. 2012, 4(3), pp. 310-318.
Barclay, A.N., et al., "The Interaction Between Signal Regulatory Protein Alpha (SIRPa) and CD47; Structure, Function, and Therapeutic Target", *Annu. Rev. Immunol.*, 2014, vol. 32, pp. 25-50.

\* cited by examiner

ANTI-SIRPα ANTIBODIES

FIELD OF THE INVENTION

The present invention relates to antibodies against SIRPα and the use of these antibodies in the treatment of cancer, optionally in combination with other anti-cancer therapeutics.

BACKGROUND OF THE PRESENT INVENTION

Since the late 1990s, therapeutic antibodies have been available for the treatment of cancer. These therapeutic antibodies can act upon malignant cells via different pathways. The signalling pathways triggered by binding of the antibody to its target on malignant cells result in inhibition of cell proliferation or in apoptosis. The Fc region of the therapeutic antibody can trigger complement dependent cytotoxicity (CDC), antibody-dependent cellular cytotoxicity (ADCC) and antibody-dependent cellular phagocytosis (ADCP). However, therapeutic antibodies are often not effective enough as monotherapy. One option to improve the efficacy of therapeutic antibodies is through improving ADCC and/or ADCP. This has been done by improving the affinity of the Fc region for Fcγ receptors, e.g. by amino acid substitutions (Richards et al. *Mol. Cancer Ther.* 2008, 7(8), 2517-2527) or by influencing the glycosylation of the Fc region (Hayes et al. *J. Inflamm. Res.* 2016, 9, 209-219).

Another way of improving the ADCC and/or ADCP of a therapeutic antibody is by combining the therapeutic antibody with an antagonistic antibody against signal regulatory protein α (anti-SIRPα) or an anti-CD47 antibody (WO2009/131453). When CD47 binds to the inhibitory immunoreceptor SIRPα expressed on monocytes, macrophages, dendritic cells and neutrophils, SIRPα transmits an inhibitory signal that prevents destruction of cancer cells by phagocytosis or other Fc-receptor-dependent cell destruction mechanisms of immune effector cells.

Tumour cells use up-regulation of CD47 as a mechanism to evade the anti-tumour immune response induced by a therapeutic antibody. Anti-CD47 or anti-SIRPα antibodies block the inhibitory signalling generated via the CD47-SIRPα axis, resulting in an increase in ADCC and/or ADCP.

Most clinical research related to the CD47-SIRPα interaction has been focused on anti-CD47 antibodies, both as monotherapy and as therapy in combination with a therapeutic antibody (Weiskopf. *Eur. J. Cancer* 2017, 76, 100-109). Research regarding anti-CD47 antibodies as anti-cancer therapeutics is growing, despite the fact that CD47 is also expressed on the surface of cells in most normal tissues.

Little research has been conducted on anti-cancer monotherapy or combination therapy using anti-SIRPα antibodies. The majority of the work on anti-SIRPα antibodies is mechanistic research regarding the CD47-SIRPα interaction and has been performed using murine anti-SIRPα antibodies; e.g. murine 12C4 and 1.23A increased neutrophil mediated ADCC of trastuzumab opsonised SKBR3 cells (Zhao et al. *PNAS* 2011, 108(45), 18342-18347). WO2015/138600 discloses murine anti-human SIRPα antibody KWAR23 and its chimeric Fab fragment, which increased the in vitro phagocytosis of i.a. cetuximab. Humanized KWAR23 with a human $IgG_1$ Fc part comprising a N297A mutation is disclosed in WO2018/026600. WO2013/056352 discloses $IgG_4$ 29AM4-5 and other $IgG_4$ human anti-SIRPα antibodies. The $IgG_4$ 29AM4-5, dosed three times per week for four weeks at 8 mg/kg, reduced leukaemic engraftment of primary human AML cells injected into the right femur of NOD scid gamma (NSG) mice.

SIRPα is a member of the family of signal regulatory proteins (SIRP), transmembrane glycoproteins with extracellular Ig-like domains present on immune effector cells. The NH2-terminal ligand binding domain of SIRPα is highly polymorphic (Takenaka et al. *Nature Immun.* 2007, 8(12), 1313-1323). However, this polymorphism does not influence binding to CD47 significantly. $SIRPα_{BIT}$ (v1) and $SIRPα_1$ (v2) are the two most common and most divergent (13 residues different) polymorphs (Hatherley et al. *J. Biol. Chem.* 2014, 289(14), 10024-10028). Other biochemically characterized human SIRP family members are $SIRPβ_1$, and SIRPγ.

$SIRPβ_1$ does not bind CD47 (van Beek et al. *J. Immunol.* 2005, 175 (12), 7781-7787, 7788-7789) and at least two $SIRPβ_1$ polymorphic variants are known, $SIRPβ_{1v1}$ (ENSP00000371018) and $SIRPβ_{1v2}$ (ENSP00000279477). Although the natural ligand of $SIRPβ_1$ is yet unknown, in vitro studies using anti-$SIRPβ_1$ specific antibodies show that engagement of $SIRPβ_1$ promotes phagocytosis in macrophages by inducing the tyrosine phosphorylation of DAP12, Syk, and SLP-76, and the subsequent activation of a MEK-MAPK-myosin light chain kinase cascade (Matozaki et al. *J. Biol. Chem.* 2004, 279(28), 29450-29460).

SIRPγ is expressed on T-cells and activated NK-cells and binds CD47 with a 10-fold lower affinity as compared to SIRPα. The CD47-SIRPγ interaction is involved in the contact between antigen-presenting cells and T-cells, co-stimulating T-cell activation and promoting T-cell proliferation (Piccio et al. *Blood* 2005, 105, 2421-2427). Furthermore, CD47-SIRPγ interactions play a role in the transendothelial migration of T-cells (Stefanisakis et al. *Blood* 2008, 112, 1280-1289).

The anti-SIRPα antibodies known in the art are less suitable for use in SIRPα-directed mono- or combination therapy, because they are either not specific for human SIRPα, or they are too specific. The prior art antibodies KWAR23, SE5A5, 29AM4-5 and 12C4 are not specific, as they also bind to human SIRPγ. Binding to SIRPγ, which is expressed on T-cells, might negatively influence T-cell proliferation and recruitment. Other anti-SIRPα antibodies have a too limited specificity, e.g. 1.23A mAb only recognizes the human SIRPα polymorphic variant $SIRPα_1$ and not the variant $SIRPα_{BIT}$, which is predominant in at least the Caucasian population (X. W. Zhao et al. *PNAS* 2011, 108(45), 18342-18347).

Besides using anti-SIRPα antibodies to increase ADCC of a therapeutic antibody, these antibodies may also be used to directly target SIRPα-expressing cancer types. Anti-SIRPα antibodies comprising wild-type human -Fc may be suitable to treat cancers expressing SIRPα, such as renal cell carcinoma and malignant melanoma, as murine anti-SIRPα antibodies having a functional Fc region slowed tumour formation in mice injected with Renca cells and B16BL6 melanoma cells, both expressing SIRPα (Yanagita et al. *JCI Insight* 2017, 2(1), e89140).

In conclusion, a need remains for anti-SIRPα antibodies which have low binding to SIRPγ, which bind specifically to both $SIRPα_1$ and $SIRPα_{BIT}$ polymorphic variants and which are suitable for use in anti-cancer therapy either alone or in combination with therapeutic antibodies.

BRIEF DESCRIPTION OF THE PRESENT INVENTION

The present invention relates to antibodies against SIRPα that are suitable for use in anti-cancer therapy. The invention further relates to the use of the antibodies in the treatment of human solid tumours and haematological malignancies.

DETAILED DESCRIPTION OF THE PRESENT INVENTION

Figure 1:
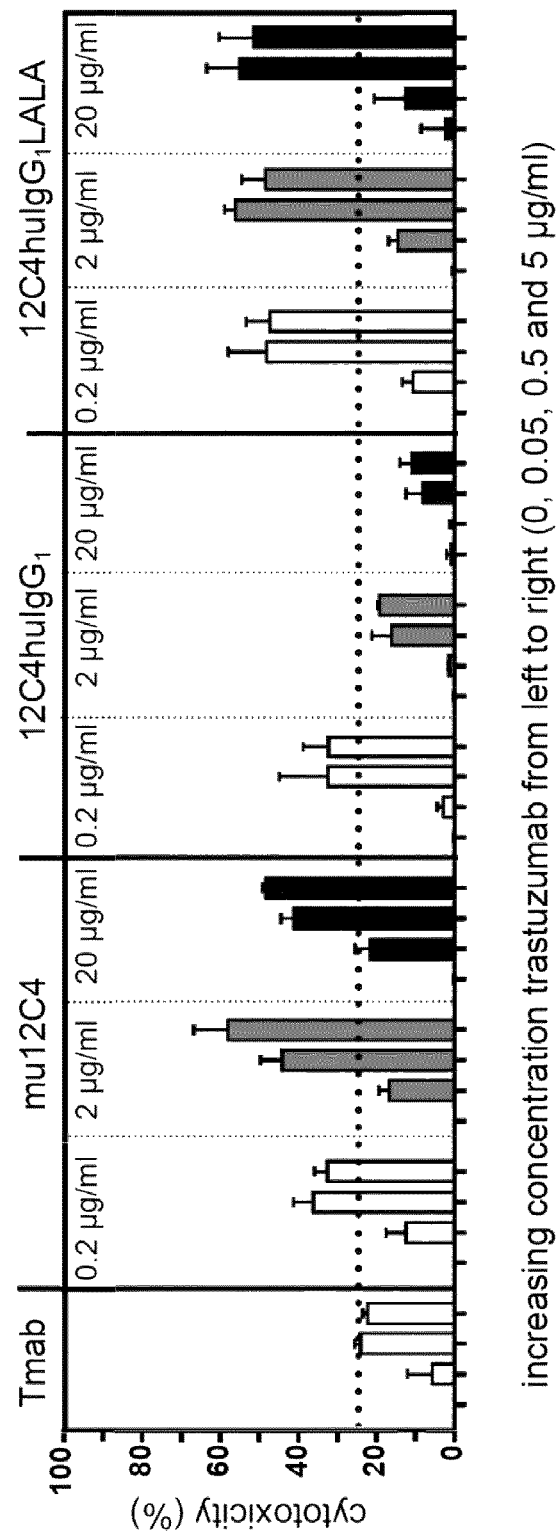
FIG. 1. Comparison of the ADCC measured in % cytotoxicity of trastuzumab (Tmab) alone, trastuzumab in combination with the murine 12C4 anti-SIRPα antibody (mu12C4), trastuzumab in combination with an antibody wherein murine 12C4 variable regions are grafted onto the human IgG$_1$ constant region (12C4huIgG$_1$), and trastuzumab in combination with an antibody wherein murine 12C4 variable regions are grafted onto the human IgG$_1$ constant region comprising the amino acid substitutions L234A and L235A (12C4huIgG$_1$LALA), measured on SKBR3 HER2-positive breast cancer cells using human neutrophils as effector cells.

No approved therapeutics directed against SIRPα are available, although this target has been shown to play an important role in tumour immune evasion mechanisms. In addition, SIRPα is expressed on various malignant cells, rendering it a potential tumour associated antigen.

The present invention relates to antagonistic anti-SIRPα antibodies which exhibit specific binding to the two predominant SIRPα polymorphic variants SIRPα$_{BIT}$ and SIRPα$_1$, that do not bind to SIRPγ and that increase the ADCC and/or ADCP of therapeutic antibodies.

The term "antibody" as used throughout the present specification refers to a monoclonal antibody (mAb) comprising two heavy chains and two light chains. Antibodies may be of any isotype such as IgA, IgE, IgG, or IgM antibodies. Preferably, the antibody is an IgG antibody, more preferably an IgG$_1$ or IgG$_2$ antibody. The antibodies may be chimeric, humanized or human. Preferably, the antibodies of the invention are humanized. Even more preferably, the antibody is a humanized or human IgG antibody, most preferably a humanized or human IgG$_1$ mAb. The antibody may have κ (kappa) or λ (lambda) light chains, preferably κ (kappa) light chains, i.e., a humanized or human IgG$_1$-κ antibody. The antibodies may comprise a constant region that is engineered, i.e. one or more mutations may be introduced to e.g. increase half-life, and/or increase or decrease effector function.

The terms "monoclonal antibody" and "mAb" as used herein refer to an antibody obtained from a population of substantially homogenous antibodies, i.e., the individual antibodies comprising the population are identical except for possible naturally-occurring mutations that may be present in minor amounts. Antibodies may be generated by immunizing animals with a mixture of peptides representing the desired antigen. B-lymphocytes are isolated and fused with myeloma cells or single B-lymphocytes are cultivated for several days in the presence of conditioned medium and feeder cells. The myeloma or B-lymphocyte supernatants containing the produced antibodies are tested to select suitable B-lymphocytes or hybridomas. Monoclonal antibodies may be prepared from suitable hybridomas by the hybridoma methodology first described by Köhler et al. *Nature* 1975, 256, 495-497. Alternatively, the RNA of suitable B-cells or lymphoma may be lysed, RNA may be isolated, reverse transcribed and sequenced. Antibodies may be made by recombinant DNA methods in bacterial, eukaryotic animal or plant cells (see, e.g., U.S. Pat. No. 4,816,567). The "monoclonal antibodies" may also be isolated from phage antibody libraries using the techniques described in the art, e.g. in Clackson et al. *Nature* 1919, 352, 624-628 and Marks et al. *J. Mol. Biol.* 1991, 222, 581-597.

The term "antigen-binding fragment" as used throughout the present specification includes a Fab, Fab' or F(ab')$_2$ fragment, a single chain (sc) antibody, a scFv, a single domain (sd) antibody, a diabody, or a minibody.

In humanized antibodies, the antigen-binding complementarity determining regions (CDRs) in the variable regions (VRs) of the heavy chain (HC) and light chain (LC) are derived from antibodies from a non-human species, commonly mouse, rat or rabbit. These non-human CDRs are combined with human framework regions (FR1, FR2, FR3 and FR4) of the variable regions of the HC and LC, in such a way that the functional properties of the antibodies, such as binding affinity and specificity, are retained. Selected amino acids in the human FRs may be exchanged for the corresponding original non-human species amino acids to improve binding affinity, while retaining low immunogenicity. Alternatively, selected amino acids of the original non-human species FRs are exchanged for their corresponding human amino acids to reduce immunogenicity, while retaining the antibody's binding affinity. The thus humanized variable regions are combined with human constant regions.

The CDRs may be determined using the approach of Kabat (in Kabat, E. A. et al., *Sequences of Proteins of Immunological Interest*, 5th Ed. Public Health Service, National Institutes of Health, Bethesda, Md., NIH publication no. 91-3242, pp. 662, 680, 689 (1991)), Chothia (Chothia et al., *Nature* 1989, 342, 877-883) or IMGT (Lefranc, *The Immunologist* 1999, 7, 132-136). In the context of the present invention, Eu numbering is used for indicating the positions in the heavy chain and light chain constant regions of the antibody. The expression "Eu numbering" refers to the Eu index as in Kabat, E. A. et al., Sequences of Proteins of Immunological Interest, 5th Ed. Public Health Service, National Institutes of Health, Bethesda, Md., NIH publication no. 91-3242, pp. 662, 680, 689 (1991).

Antagonistic antibodies have affinity for a specific antigen, and binding of the antibody to its antigen inhibits the function of an agonist or inverse agonist at receptors. In the present case, binding of an antagonistic anti-SIRPα antibody to SIRPα will either prevent binding of CD47 to SIRPα or disrupt the inhibitory signal that is triggered by the CD47-SIRPα binding.

Antagonistic anti-SIRPα antibodies may bind to the same site where CD47 binds, preventing ligation of SIRPα by CD47 and consequently inhibiting the signalling that negatively regulates the Fc-receptor-dependent action of immune effector cells. Antagonistic anti-SIRPα antibodies may also bind to a site of SIRPα that is different from the binding site of CD47, i.e. an allosteric site, and inhibit the inhibitory signalling of SIRPα without direct interference with the physical CD47-SIRPα interaction, e.g. a change in the three-dimensional shape of SIRPα. This change in the three-dimensional shape prevents (downstream) signalling upon binding to CD47. When SIRPα is bound at an allosteric site, CD47 may still be bound by SIRPα, which might cause CD47 to be less available for binding to thrombospondin-1 (TSP-1). Ligation of TSP-1 to CD47 plays a role in e.g. negative regulation of T-cell activation (Soto-Pantoja et al. *Crit. Rev. Biochem. Mol. Biol.* 2015, 50(3), 212-230).

The term "binding affinity" as used throughout the present specification, refers to the dissociation constant ($K_D$) of a particular antigen-antibody interaction. The $K_D$ is the ratio of the rate of dissociation ($k_{off}$) to the association rate ($k_{on}$). Consequently, $K_D$ equals $k_{off}/k_{on}$, and is expressed as a molar concentration (M). It follows that the smaller the $K_D$, the stronger the affinity of binding. Typically, $K_D$ values are determined by using surface plasmon resonance (SPR), typically using a biosensor system (e.g. Biacore®) using methods known in the art (e.g. E. S. Day et al. *Anal. Biochem.* 2013, 440, 96-107). The term "binding affinity" may also refer to the concentration of antibody that gives half-maximal binding ($EC_{50}$) determined with e.g. an ELISA assay or as determined by flow cytometry.

The term "specific binding" as used throughout the present specification relates to binding between an antibody and its antigen with a $K_D$ of typically less than $10^{-7}$ M, such as $10^{-8}$M, $10^{-9}$ M, $10^{-10}$ M, $10^{-11}$ M or even lower as determined by SPR at 25° C.

The term "low affinity" as used throughout the present specification is interchangeable with the phrases "does/do not bind" or "is/are not binding to", and refers to a binding affinity between an antibody and its antigen with an $EC_{50}$ larger than 1500 ng/ml as determined using an ELISA assay, or where no specific binding is observed between the immobilized antigen and the antibody as determined by SPR.

The term "high affinity" as used throughout the present specification and refers to a binding affinity between an antibody and its antigen with a $K_D$ of typically less than $10^{-10}$ M, $10^{-11}$ M or even lower as determined by SPR at 25° C.

In particular, the present invention relates to an anti-SIRPα antibody or an antigen-binding fragment thereof comprising heavy chain (HC) and light chain (LC) variable region (VR) complementarity determining regions (CDRs) selected from the group consisting of:

a. CDR1, CDR2 and CDR3 amino acid sequences of SEQ ID NO:1 and CDR1, CDR2 and CDR3 amino acid sequences of SEQ ID NO:2;
b. CDR1, CDR2 and CDR3 amino acid sequences of SEQ ID NO:3 and CDR1, CDR2 and CDR3 amino acid sequences of SEQ ID NO:4;
c. CDR1, CDR2 and CDR3 amino acid sequences of SEQ ID NO:5 and CDR1, CDR2 and CDR3 amino acid sequences of SEQ ID NO:6;
d. CDR1, CDR2 and CDR3 amino acid sequences of SEQ ID NO:7 and CDR1, CDR2 and CDR3 amino acid sequences of SEQ ID NO:8;
e. CDR1, CDR2 and CDR3 amino acid sequences of SEQ ID NO:9 and CDR1, CDR2 and CDR3 amino acid sequences of SEQ ID NO:10;
f. CDR1, CDR2 and CDR3 amino acid sequences of SEQ ID NO:11 and CDR1, CDR2 and CDR3 amino acid sequences of SEQ ID NO:12;
g. CDR1, CDR2 and CDR3 amino acid sequences of SEQ ID NO:13 and CDR1, CDR2 and CDR3 amino acid sequences of SEQ ID NO:14;
h. CDR1, CDR2 and CDR3 amino acid sequences of SEQ ID NO:15 and CDR1, CDR2 and CDR3 amino acid sequences of SEQ ID NO:16; and
i. CDR1, CDR2 and CDR3 amino acid sequences of SEQ ID NO:17 and CDR1, CDR2 and CDR3 amino acid sequences of SEQ ID NO:18, wherein the CDRs are determined according to Kabat numbering.

Preferably, the present invention relates to an anti-SIRPα antibody or an antigen-binding fragment thereof comprising heavy chain (HC) and light chain (LC) variable region (VR) complementarity determining regions (CDRs) selected from the group consisting of:

a. CDR1, CDR2 and CDR3 amino acid sequences of SEQ ID NO:3 and CDR1, CDR2 and CDR3 amino acid sequences of SEQ ID NO:4;
b. CDR1, CDR2 and CDR3 amino acid sequences of SEQ ID NO:5 and CDR1, CDR2 and CDR3 amino acid sequences of SEQ ID NO:6;
c. CDR1, CDR2 and CDR3 amino acid sequences of SEQ ID NO:7 and CDR1, CDR2 and CDR3 amino acid sequences of SEQ ID NO:8;
d. CDR1, CDR2 and CDR3 amino acid sequences of SEQ ID NO:9 and CDR1, CDR2 and CDR3 amino acid sequences of SEQ ID NO:10;
e. CDR1, CDR2 and CDR3 amino acid sequences of SEQ ID NO:11 and CDR1, CDR2 and CDR3 amino acid sequences of SEQ ID NO:12;
f. CDR1, CDR2 and CDR3 amino acid sequences of SEQ ID NO:13 and CDR1, CDR2 and CDR3 amino acid sequences of SEQ ID NO:14;
g. CDR1, CDR2 and CDR3 amino acid sequences of SEQ ID NO:15 and CDR1, CDR2 and CDR3 amino acid sequences of SEQ ID NO:16; and
h. CDR1, CDR2 and CDR3 amino acid sequences of SEQ ID NO:17 and CDR1, CDR2 and CDR3 amino acid sequences of SEQ ID NO:18, wherein the CDRs are determined according to Kabat numbering.

More preferably, the present invention relates to an anti-SIRPα antibody or an antigen-binding fragment thereof comprising HCVR and LCVR CDRs selected from the group consisting of:

a. CDR1, CDR2 and CDR3 amino acid sequences of SEQ ID NO:3 and CDR1, CDR2 and CDR3 amino acid sequences of SEQ ID NO:4;

b. CDR1, CDR2 and CDR3 amino acid sequences of SEQ ID NO:5 and CDR1, CDR2 and CDR3 amino acid sequences of SEQ ID NO:6;
c. CDR1, CDR2 and CDR3 amino acid sequences of SEQ ID NO:7 and CDR1, CDR2 and CDR3 amino acid sequences of SEQ ID NO:8;
d. CDR1, CDR2 and CDR3 amino acid sequences of SEQ ID NO:9 and CDR1, CDR2 and CDR3 amino acid sequences of SEQ ID NO:10; and
e. CDR1, CDR2 and CDR3 amino acid sequences of SEQ ID NO:13 and CDR1, CDR2 and CDR3 amino acid sequences of SEQ ID NO:14, wherein the CDRs are determined according to Kabat numbering.

Even more preferably, the present invention relates to an anti-SIRPα antibody or an antigen-binding fragment thereof comprising HCVR and LCVR CDRs selected from the group consisting of:

a. CDR1, CDR2 and CDR3 amino acid sequences of SEQ ID NO:5 and CDR1, CDR2 and CDR3 amino acid sequences of SEQ ID NO:6;
b. CDR1, CDR2 and CDR3 amino acid sequences of SEQ ID NO:7 and CDR1, CDR2 and CDR3 amino acid sequences of SEQ ID NO:8; and
c. CDR1, CDR2 and CDR3 amino acid sequences of SEQ ID NO:13 and CDR1, CDR2 and CDR3 amino acid sequences of SEQ ID NO:14, wherein the CDRs are determined according to Kabat numbering.

Most preferably, the present invention relates to an anti-SIRPα antibody or an antigen-binding fragment thereof comprising HCVR and LCVR CDRs selected from the group consisting of:

a. CDR1, CDR2 and CDR3 amino acid sequences of SEQ ID NO:7 and CDR1, CDR2 and CDR3 amino acid sequences of SEQ ID NO:8; and
b. CDR1, CDR2 and CDR3 amino acid sequences of SEQ ID NO:13 and CDR1, CDR2 and CDR3 amino acid sequences of SEQ ID NO:14, wherein the CDRs are determined according to Kabat numbering.

In a preferred embodiment, the present invention relates to an anti-SIRPα antibody or an antigen-binding fragment thereof as defined hereinabove, wherein the antibody shows specific binding to both SIRPα$_{BIT}$ and SIRPα$_1$ and does not bind to SIRPγ.

In a more preferred embodiment, the anti-SIRPα antibody or an antigen-binding fragment thereof specifically binds SIRPα$_{BIT}$ with a K$_D$ below $10^{-9}$ M and binds SIRPα$_1$ with a K$_D$ below $10^{-7}$ M, wherein the K$_D$ is measured with SPR at 25° C. Preferably, the anti-SIRPα antibody or an antigen-binding fragment thereof binds SIRPα$_1$ with a K$_D$ below $10^{-8}$ M.

In another more preferred embodiment, the anti-SIRPα antibody or an antigen-binding fragment thereof specifically binds SIRPα$_{BIT}$ and SIRPα$_1$ with a K$_D$ below $10^{-9}$ M, wherein the K$_D$ is measured with SPR at 25° C.

In an even more preferred embodiment, the anti-SIRPα antibody or an antigen-binding fragment thereof specifically binds SIRPα$_{BIT}$ and SIRPα$_1$ with a K$_D$ below $10^{-10}$ M. Preferably, the anti-SIRPα or an antigen-binding fragment thereof antibody specifically binds SIRPα$_{BIT}$ with a K$_D$ below $10^{-10}$ M and SIRPα$_1$ with a K$_D$ below $10^{-11}$ M. Typically, the anti-SIRPα antibody as defined hereinabove is a chimeric, humanized or human antibody. Preferably, the anti-SIRPα antibody is a humanized or human antibody. More preferably, the anti-SIRPα antibody is a humanized antibody. In a particular embodiment, the humanized anti-SIRPα antibody or an antigen-binding fragment thereof according to the invention comprises a HCVR and a LCVR selected from the group consisting of:

a. HCVR amino acid sequence of SEQ ID NO:30 and LCVR amino acid sequence of SEQ ID NO:31;
b. HCVR amino acid sequence of SEQ ID NO:32 and LCVR amino acid sequence of SEQ ID NO:33;
c. HCVR amino acid sequence of SEQ ID NO:34 and LCVR amino acid sequence of SEQ ID NO:8;
d. HCVR amino acid sequence of SEQ ID NO:35 and LCVR amino acid sequence of SEQ ID NO:36;
e. HCVR amino acid sequence of SEQ ID NO:35 and LCVR amino acid sequence of SEQ ID NO:37;
f. HCVR amino acid sequence of SEQ ID NO:13 and LCVR amino acid sequence of SEQ ID NO:38; and
g. HCVR amino acid sequence of SEQ ID NO:13 and LCVR amino acid sequence of SEQ ID NO:37.

In a preferred embodiment, the humanized anti-SIRPα antibody or an antigen-binding fragment thereof comprises HCVR amino acid sequence of SEQ ID NO:30 and LCVR amino acid sequence of SEQ ID NO:31.

In another preferred embodiment, the humanized anti-SIRPα antibody or an antigen-binding fragment thereof comprises HCVR amino acid sequence of SEQ ID NO:32 and LCVR amino acid sequence of SEQ ID NO:33.

In yet another preferred embodiment, the humanized anti-SIRPα antibody or an antigen-binding fragment thereof comprises HCVR amino acid sequence of SEQ ID NO:34 and LCVR amino acid sequence of SEQ ID NO:8.

In yet another preferred embodiment, the humanized anti-SIRPα antibody or an antigen-binding fragment thereof comprises HCVR amino acid sequence of SEQ ID NO:35 and LCVR amino acid sequence of SEQ ID NO:36.

In yet another preferred embodiment, the humanized anti-SIRPα antibody or an antigen-binding fragment thereof comprises HCVR amino acid sequence of SEQ ID NO:35 and LCVR amino acid sequence of SEQ ID NO:37.

In yet another preferred embodiment, the humanized anti-SIRPα antibody or an antigen-binding fragment thereof comprises HCVR amino acid sequence of SEQ ID NO:13 and LCVR amino acid sequence of SEQ ID NO:38.

In yet another preferred embodiment, the humanized anti-SIRPα antibody or an antigen-binding fragment thereof comprises HCVR amino acid sequence of SEQ ID NO:13 and LCVR amino acid sequence of SEQ ID NO:37.

Besides binding to both human (hu)SIRPα$_{BIT}$ and (hu)SIRPα$_1$, the antibodies according to the invention may also bind to cynomolgus monkey (cy)SIRPα, enabling in vivo studies in a relevant animal model.

The antibodies according to the invention may bind to a site of SIRPα that is different from the binding site of CD47, i.e. an allosteric site and inhibit the inhibitory signalling of SIRPα without direct interference with the physical CD47-SIRPα interaction. Alternatively, the antibodies may bind to the same site where CD47 binds, preventing ligation of SIRPα by CD47 and consequently inhibiting the signalling that negatively regulates the Fc-receptor-dependent action of immune effector cells.

The anti-SIRPα antibodies or antigen-binding fragments thereof as described hereinabove are more specific than known anti-SIRPα antibodies, and show excellent affinity for both SIRPα$_{BIT}$ and SIRPα$_1$. As well, the anti-SIRPα antibodies according to the invention do not bind to SIRPγ.

In one particular embodiment, the anti-SIRPα antibody according to the invention comprises an Fc region that binds to activating Fc receptors present on human immune effector cells. Such anti-SIRPα antibody is suitable for monotherapy of SIRPα-positive human solid tumours and haematological malignancies as it can induce ADCC and/or ADCP. Human immune effector cells possess a variety of activating Fc receptors, which upon ligation trigger phagocytosis, cytokine release, ADCC and/or ADCP, etc. Examples of these receptors are Fcγ receptors, e.g. FcγRI (CD64), FcγRIIA (CD32), FcγRIIIA (CD16a), FcγRIIIB (CD16b), FcγRIIC and the Fcα receptor FcαRI (CD89). The various natural antibody isotypes bind to these receptors. E.g. $IgG_1$ binds to FcγRI, FcγRIIA, FcγRIIC, FcγRIIIA, FcγRIIIB; $IgG_2$ binds to FcγRIIA, FcγRIIC, FcγRIIIA; $IgG_3$ binds to FcγRI, FcγRIIA, FcγRIIC, FcγRIIIA, FcγRIIIB; $IgG_4$ binds to FcγRI, FcγRIIA, FcγRIIC, FcγRIIIA; and IgA binds to FcαRI.

In a preferred embodiment, the anti-SIRPα antibody according to the invention comprises an Fc region of the IgA or IgG isotype. More preferred is an anti-SIRPα antibody comprising an Fc region of the $IgG_1$, $IgG_2$, $IgG_3$ or $IgG_4$ isotype; the $IgG_1$, $IgG_2$ or $IgG_4$ isotype is even more preferred. Most preferred is an anti-SIRPα antibody comprising an Fc region of the $IgG_1$ isotype.

Although the anti-SIRPα antibodies comprising an Fc region that binds to activating Fc receptors present on human immune effector cells may be suitable to treat cancers expressing SIRPα, chimeric anti-SIRPα $IgG_1$ antibodies did not show the expected results when tested in vitro in combination with other antibodies that comprise a human Fc region that binds to activating Fc receptors present on human immune effector cells (i.e. antibodies that are able to induce ADCC and/or ADCP). Results of in vitro ADCC assays showed that a chimeric $IgG_1$ anti-SIRPα antibody does not increase the ADCC of such other antibody as much as expected on the basis of earlier results using murine antibodies.

Therefore, the invention relates to anti-SIRPα antibodies that exhibit reduced binding to or low affinity for activating Fc receptors present on human immune effector cells. Such anti-SIRPα antibodies comprise a modified Fc region in which one or more amino acids have been substituted by (an)other amino acid(s) when compared to a similar unmodified Fc region. Reduced binding means that the affinity of the anti-SIRPα antibody comprising a modified Fc region for the activating Fc receptors is less than the affinity of an anti-SIRPα antibody with the same variable regions comprising a similar unmodified Fc region. The binding affinity of antibodies for activating Fc receptors is typically measured using Surface Plasmon Resonance (SPR) or flow cytometry using methods known in the art, e.g. the method of Harrison et al. in *J. Pharm. Biomed. Anal.* 2012, 63, 23-28. Antibodies exhibiting reduced binding to or low affinity for the human Fcα or Fcγ receptor in combination with a therapeutic antibody are especially effective in cellular destruction of cancer cells by increasing ADCC and/or ADCP of effector immune effector cells. Typically, the Fc region of the anti-SIRPα antibody according to the invention is modified to reduce binding to activating Fc receptors present on human immune effector cells.

Therefore, the anti-SIRPα antibody according to the invention comprises a modified Fc region that exhibits reduced binding to or low affinity for a human Fcα or Fcγ receptor. For instance, the $IgG_1$ binding to an Fcγ receptor can be reduced by substituting one or more $IgG_1$ amino acids selected from the group consisting of L234, L235, G237, D265, D270, N297, A327, P328, and P329 (Eu numbering); the $IgG_2$ binding can be reduced by introducing e.g. one or more of the following amino acid substitutions V234A, G237A, P238S, H268A, V309L, A330S, and P331S; or H268Q, V309L, A330S, and P331S (numbering analogue to $IgG_1$ Eu numbering) (Vafa et al. *Methods* 2014, 65, 114-126); the $IgG_3$ binding can be reduced by introducing e.g. the amino acid substitutions L234A and L235A, or the amino acid substitutions L234A, L235A and P331S (Leoh et al. *Mol. Immunol.* 2015, 67, 407-415); and the $IgG_4$ binding can be reduced by introducing e.g. the amino acid substitutions S228P, F234A and L235A ((numbering analogue to $IgG_1$ Eu numbering) (Parekh et al. *mAbs* 2012, 4(3), 310-318). IgA binding to the Fcα receptor can be reduced by introducing e.g. one or more of the amino acid substitutions L257R, P440A, A442R, F443R, and P440R (sequential numbering, Pleass et al. *J. Biol. Chem.* 1999, 271(33), 23508-23514).

Preferably, the anti-SIRPα antibody according to the invention comprises a modified Fc region that exhibits reduced binding to or low affinity for a human Fcγ receptor. More preferably, the modified Fc region is an Fc region of the IgG isotype. Even more preferably, the modified Fc region is an Fc region of the $IgG_1$, $IgG_2$ or $IgG_4$ isotype.

In a preferred embodiment, the anti-SIRPα antibody according to the invention comprises a modified human $IgG_1$ Fc region comprising one or more amino acid substitutions at one or more positions selected from the group consisting of L234, L235, G237, D265, D270, N297, A327, P328, and P329 (Eu numbering).

Preferably, the anti-SIRPα antibody comprises a modified Fc $IgG_1$ region, which does not comprise either amino acid substitution N297A or N297G. More preferably, the anti-SIRPα antibody comprises a modified Fc $IgG_1$ region, which does not comprise an amino acid substitution at position N297.

In one embodiment, the modified human $IgG_1$ Fc region comprises one or more amino acid substitutions selected from the group consisting of L234A, L234E, L235A, G237A, D265A, D265E, D265N, D270A, D270E, D270N, N297A, N297G, A327Q, P328A, P329A and P329G. Preferably, the one or more amino acid substitutions are selected from the group consisting of L234A, L234E, L235A, G237A, D265A, D265E, D265N, N297A, P328A, P329A and P329G.

In another embodiment, the modified human $IgG_1$ Fc region comprises one or more amino acid substitutions selected from the group consisting of L234A, L234E, L235A, G237A, D265A, D265E, D265N, D270A, D270E, D270N, A327Q, P328A, P329A and P329G. Preferably, the one or more amino acid substitutions are selected from the group consisting of L234A, L234E, L235A, G237A, D265A, D265E, D265N, P328A, P329A and P329G. More preferably, the modified Fc $IgG_1$ region does not comprise either amino acid substitution N297A or N297G. Even more preferably, the modified Fc $IgG_1$ region does not comprise an amino acid substitution at position N297.

In a preferred embodiment, the modified human $IgG_1$ Fc region comprises the amino acid substitutions L234A and L235A, L234E and L235A, L234A, L235A and P329A or L234A, L235A and P329G. Preferably, the modified Fc $IgG_1$ region does not comprise either amino acid substitution N297A or N297G. More preferably, the modified Fc $IgG_1$ region does not comprise an amino acid substitution at position N297.

In another preferred embodiment, the anti-SIRPα antibody according to the invention comprises a modified human $IgG_1$ Fc region comprising the amino acid substitutions L234A and L235A or L234E and L235A, preferably amino acid substitutions L234A and L235A. More preferably, the modified Fc IgG$_1$ region does not comprise either amino acid substitution N297A or N297G. Even more preferably, the modified Fc IgG$_1$ region does not comprise an amino acid substitution at position N297.

The present invention further relates to a pharmaceutical composition comprising an anti-SIRPα antibody as described hereinabove and one or more pharmaceutically acceptable excipients. Typical pharmaceutical formulations of therapeutic proteins such as antibodies take the form of lyophilized cakes (lyophilized powders), which require (aqueous) dissolution (i.e. reconstitution) before intravenous infusion, or frozen (aqueous) solutions, which require thawing before use.

Typically, the pharmaceutical composition is provided in the form of a lyophilized cake. Suitable pharmaceutically acceptable excipients for inclusion into the pharmaceutical composition (before freeze-drying) in accordance with the present invention include buffer solutions (e.g. citrate, histidine or succinate containing salts in water), lyoprotectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage.

The present invention further relates to an anti-SIRPα antibody or pharmaceutical composition as described hereinabove for use as a medicament.

In one embodiment, the present invention relates to an anti-SIRPα antibody or pharmaceutical composition as described hereinabove for use in the treatment of human solid tumours and haematological malignancies. The anti-SIRPα antibodies of the invention may be used in the treatment of solid tumours, such as breast cancer, renal cancer, or melanoma, or haematological malignancies, such as Acute Myeloid Leukaemia (AML).

In a second embodiment, the invention relates to an anti-SIRPα antibody comprising an Fc region that binds to activating Fc receptors present on human immune effector cells for use in the treatment of SIRPα-positive human solid tumours and haematological malignancies. Preferably, the Fc region that binds to activating Fc receptors present on human immune effector cells is of the IgA or IgG isotype. More preferred is an anti-SIRPα antibody comprising an Fc region of the IgG$_1$, IgG$_2$, IgG$_3$ or IgG$_4$ isotype; the IgG$_1$, IgG$_2$ or IgG$_4$ isotype is even more preferred. Most preferred is an anti-SIRPα antibody comprising an Fc region of the IgG$_1$ isotype for use in the treatment of SIRPα-positive human solid tumours and haematological malignancies.

In a third embodiment, the present invention relates to an anti-SIRPα antibody or pharmaceutical composition as described hereinabove for use in the treatment of human solid tumours and haematological malignancies in combination with the use of one or more other anti-cancer therapies. Suitable anti-cancer therapies are surgery, chemotherapy, radiation therapy, hormonal therapy, targeted therapy and immunotherapy. The anti-SIRPα antibody or pharmaceutical composition as described hereinabove may be for concomitant or sequential use in the treatment of human solid tumours and haematological malignancies in combination with the use of one or more other anti-cancer therapies. In particular, the anti-SIRPα antibody or pharmaceutical composition as described hereinabove may be for use in the treatment of human solid tumours and haematological malignancies after the use of one or more other anti-cancer therapies.

Preferably, the present invention relates to an anti-SIRPα antibody or pharmaceutical composition as described hereinabove for use in the treatment of human solid tumours and haematological malignancies in combination with the use of one or more other anti-cancer therapeutics. In particular, the anti-SIRPα antibody or pharmaceutical composition as described hereinabove may be for use in the treatment of human solid tumours and haematological malignancies after the use of one or more other anti-cancer therapeutics.

Suitable anti-cancer therapeutics include chemotherapeutics, radiation therapeutics, hormonal therapeutics, targeted therapeutics and immunotherapeutic agents. Suitable chemotherapeutics include alkylating agents, such as nitrogen mustards, nitrosoureas, tetrazines and aziridines; anti metabolites, such as anti-folates, fluoropyrimidines, deoxynucleoside analogues and thiopurines; anti-microtubule agents, such as vinca alkaloids and taxanes; topoisomerase I and II inhibitors; and cytotoxic antibiotics, such as anthracyclines and bleomycins.

Suitable radiation therapeutics include radio isotopes, such as $^{131}$I-metaiodobenzylguanidine (MIBG), $^{32}$P as sodium phosphate, $^{223}$Ra chloride, $^{89}$Sr chloride and $^{153}$Sm diamine tetramethylene phosphonate (EDTMP).

Suitable agents to be used as hormonal therapeutics include inhibitors of hormone synthesis, such as aromatase inhibitors and GnRH analogues; and hormone receptor antagonists, such as selective oestrogen receptor modulators and antiandrogens.

Targeted therapeutics are therapeutics that interfere with specific proteins involved in tumorigenesis and proliferation and may be small molecule drugs; proteins, such as therapeutic antibodies; peptides and peptide derivatives; or protein-small molecule hybrids, such as antibody-drug conjugates. Examples of targeted small molecule drugs include mTor inhibitors, such as everolimus, temsirolimus and rapamycin; kinase inhibitors, such as imatinib, dasatinib and nilotinib; VEGF inhibitors, such as sorafenib and regorafenib; and EGFR/HER2 inhibitors such as gefitinib, lapatinib and erlotinib. Examples of peptide or peptide derivative targeted therapeutics include proteasome inhibitors, such as bortezomib and carfilzomib.

Immunotherapeutic agents include agents that induce, enhance or suppress an immune response, such as cytokines (IL-2 and IFN-α); immuno modulatory imide drugs, such as thalidomide, lenalidomide and pomalidomide; therapeutic cancer vaccins, such as talimogene laherparepvec; cell based immunotherapeutic agents, such as dendritic cell vaccins, adoptive T-cells and chimeric antigen receptor-modified T-cells); and therapeutic antibodies that can trigger ADCC/ADCP or CDC via their Fc region when binding to membrane bound ligands on a cancer cell.

Preferably, the invention relates to an anti-SIRPα antibody or pharmaceutical composition as described hereinabove for use in the treatment of human solid tumours and haematological malignancies in combination with one or more other anti-cancer therapeutics, wherein the anti-cancer therapeutic is a targeted therapeutic or an immunotherapeutic agent. A preferred targeted therapeutic in accordance with the invention is a therapeutic antibody or an antibody-drug conjugate (ADC). The most preferred targeted therapeutic is a therapeutic antibody.

The term "therapeutic antibody" as used throughout the present specification refers to an antibody or an antigen-binding fragment thereof as defined hereinabove, which is suitable for human therapy. Antibodies suitable for human therapy are of sufficient quality, safe and efficacious for treatment of specific human diseases. Quality may be assessed using the established guidelines for Good Manufacturing Practice; safety and efficacy are typically assessed using established guidelines of medicines regulatory authorities, e.g. the European Medicines Agency (EMA) or the United States Food and Drug Administration (FDA). These guidelines are well-known in the art.

Preferably, the therapeutic antibody is an antibody approved by a medicines regulatory authority, such as the EMA or FDA. Online databases of most Regulatory Authorities can be consulted to find whether an antibody is approved.

The term "ADC" as used throughout the present specification refers to a cytotoxic drug conjugated to an antibody or an antigen-binding fragment thereof as defined hereinabove via a linker. Typically, the cytotoxic drugs are highly potent, e.g. a duocarmycin, calicheamicin, pyrrolobenzodiazepine (PBD) dimer, maytansinoid or auristatin derivative. The linker may be cleavable, e.g. comprising the cleavable dipeptide valine-citrulline (vc) or valine-alanine (va), or non-cleavable, e.g. succinimidyl-4-(N-maleimidomethyl) cyclohexane-1-carboxylate (SMCC).

Typically, the therapeutic antibody for use in combination with an anti-SIRPα antibody according to the invention is a monospecific or bispecific antibody or antibody fragment comprising at least one HCVR and LCVR binding to a target selected from the group consisting of annexin A1, B7H3, B7H4, CA6, CA9, CA15-3, CA19-9, CA27-29, CA125, CA242, CCR2, CCR5, CD2, CD19, CD20, CD22, CD30, CD33, CD37, CD38, CD40, CD44, CD47, CD56, CD70, CD74, CD79, CD115, CD123, CD138, CD203c, CD303, CD333, CEA, CEACAM, CLCA-1, CLL-1, c-MET, Cripto, CTLA-4, DLL3, EGFL, EGFR, EPCAM, EPh (e.g. EphA2 or EPhB3), endothelin B receptor (ETBR), FAP, FcRL5 (CD307), FGF, FGFR (e.g. FGFR3), FOLR1, GCC, GPNMB, HER2, HMW-MAA, integrin α (e.g. αvβ3 and αvβ5), IGF1R, TM4SF1 (or L6 antigen), Lewis A like carbohydrate, Lewis X, Lewis Y, LIV1, mesothelin, MUC1, MUC16, NaPi2b, Nectin-4, PD-1, PD-L1, PSMA, PTK7, SLC44A4, STEAP-1, 5T4 antigen (or TPBG, trophoblast glycoprotein), TF (tissue factor), Thomsen-Friedenreich antigen (TF-Ag), Tag72, TNF, TNFR, TROP2, VEGF, VEGFR, and VLA.

Preferred is a monospecific therapeutic antibody. More preferred is an antibody against a membrane-bound target on the surface of tumour cells.

Suitable therapeutic antibodies for use in combination with an anti-SIRPα antibody according to the invention include alemtuzumab, bevacizumab, cetuximab, panitumumab, rituximab, and trastuzumab.

Suitable ADCs for use in combination with an anti-SIRPα antibody according to the invention include trastuzumab emtansine and brentuximab vedotin.

In a preferred embodiment, the present invention relates to an anti-SIRPα antibody as described hereinabove for the aforementioned use in combination with a therapeutic antibody against a membrane-bound target on the surface of tumour cells which comprises a human Fc region that binds to activating Fc receptors present on human immune effector cells.

Via binding to these activating Fc receptors, described hereinabove, a therapeutic antibody comprising a human Fc region that binds to activating Fc receptors present on human immune effector cells can induce ADCC and/or ADCP. Therapeutic antibodies of the human IgG, IgE, or IgA isotype comprise a human Fc region that binds to activating Fc receptors present on human immune effector cells.

A preferred therapeutic antibody for use according to the invention is a therapeutic antibody of the IgG or IgA isotype. More preferred is a therapeutic antibody of the IgG isotype, such as $IgG_1$, $IgG_2$, $IgG_3$, and $IgG_4$ antibodies. Even more preferred is a therapeutic antibody of the $IgG_1$ or $IgG_2$ isotype. Most preferred is a therapeutic antibody of the $IgG_1$ isotype.

Preferably, the present invention relates to a humanized anti-SIRPα antibody comprising HCVR and LCVR CDRs selected from the group consisting of:

a. CDR1, CDR2 and CDR3 amino acid sequences of SEQ ID NO:1 and CDR1, CDR2 and CDR3 amino acid sequences of SEQ ID NO:2;

b. CDR1, CDR2 and CDR3 amino acid sequences of SEQ ID NO:3 and CDR1, CDR2 and CDR3 amino acid sequences of SEQ ID NO:4;

c. CDR1, CDR2 and CDR3 amino acid sequences of SEQ ID NO:5 and CDR1, CDR2 and CDR3 amino acid sequences of SEQ ID NO:6;

d. CDR1, CDR2 and CDR3 amino acid sequences of SEQ ID NO:7 and CDR1, CDR2 and CDR3 amino acid sequences of SEQ ID NO:8;

e. CDR1, CDR2 and CDR3 amino acid sequences of SEQ ID NO:9 and CDR1, CDR2 and CDR3 amino acid sequences of SEQ ID NO:10;

f. CDR1, CDR2 and CDR3 amino acid sequences of SEQ ID NO:11 and CDR1, CDR2 and CDR3 amino acid sequences of SEQ ID NO:12;

g. CDR1, CDR2 and CDR3 amino acid sequences of SEQ ID NO:13 and CDR1, CDR2 and CDR3 amino acid sequences of SEQ ID NO:14;

h. CDR1, CDR2 and CDR3 amino acid sequences of SEQ ID NO:15 and CDR1, CDR2 and CDR3 amino acid sequences of SEQ ID NO:16; and i. CDR1, CDR2 and CDR3 amino acid sequences of SEQ ID NO:17 and CDR1, CDR2 and CDR3 amino acid sequences of SEQ ID NO:18, for use in the treatment of human solid tumours and haematological malignancies in combination with the use of a therapeutic antibody against a membrane-bound target on the surface of tumour cells, which comprises a human Fc region that binds to activating Fc receptors present on human immune effector cells, wherein the anti-SIRPα antibody comprises a modified Fc region that exhibits reduced binding to a human Fcα or Fcγ receptor, when compared to the same anti-SIRPα antibody comprising a wild-type Fc region.

In a preferred embodiment, the humanized anti-SIRPα antibody for use in the treatment of human solid tumours and haematological malignancies in combination with the therapeutic antibody, comprises a modified human $IgG_1$ Fc region comprising one or more amino acid substitutions at one or more positions selected from the group consisting of L234, L235, G237, D265, D270, N297, A327, P328, and P329 (Eu numbering).

Preferably, the humanized anti-SIRPα antibody for use in the treatment of human solid tumours and haematological malignancies in combination with the therapeutic antibody comprises a modified Fc $IgG_1$ region, which does not comprise either amino acid substitution N297A or N297G. More preferably, the anti-SIRPα antibody comprises a modified Fc $IgG_1$ region, which does not comprise an amino acid substitution at position N297.

In one embodiment, the modified human $IgG_1$ Fc region comprises one or more amino acid substitutions selected from the group consisting of L234A, L234E, L235A, G237A, D265A, D265E, D265N, D270A, D270E, D270N, N297A, N297G, A327Q, P328A, P329A, and P329G.

In another embodiment, the humanized anti-SIRPα antibody for use in the treatment of human solid tumours and haematological malignancies in combination with the therapeutic antibody comprises a modified Fc IgG$_1$ region comprising one or more amino acid substitutions selected from the group consisting of L234A, L234E, L235A, G237A, D265A, D265E, D265N, D270A, D270E, D270N, A327Q, P328A, P329A and P329G. Preferably, the one or more amino acid substitutions are selected from the group consisting of L234A, L234E, L235A, G237A, D265A, D265E, D265N, P328A, P329A and P329G. More preferably, the modified Fc IgG$_1$ region does not comprise either amino acid substitution N297A or N297G. Even more preferably, the modified Fc IgG$_1$ region does not comprise an amino acid substitution at position N297.

In a preferred embodiment, the modified human IgG$_1$ Fc region comprises the amino acid substitutions L234A and L235A, L234E and L235A, L234A, L235A and P329A or L234A, L235A and P329G. Preferably, the modified Fc IgG$_1$ region does not comprise either amino acid substitution N297A or N297G. More preferably, the modified Fc IgG$_1$ region does not comprise an amino acid substitution at position N297.

In another preferred embodiment, the humanized anti-SIRPα antibody for use in the treatment of human solid tumours and haematological malignancies in combination with the therapeutic antibody comprises a modified human IgG$_1$ Fc region comprising the amino acid substitutions L234A and L235A or L234E and L235A, preferably amino acid substitutions L234A and L235A. More preferably, the modified Fc IgG$_1$ region does not comprise either amino acid substitution N297A or N297G. Even more preferably, the modified Fc IgG$_1$ region does not comprise an amino acid substitution at position N297.

In a preferred embodiment, the humanized anti-SIRPα antibody for use in the treatment of human solid tumours and haematological malignancies in combination with the use of a therapeutic antibody against a membrane-bound target on the surface of tumour cells which comprises a human Fc region that binds to activating Fc receptors present on human immune effector cells, comprises an Fc region comprising the amino acid substitutions L234A and L235A, and HCVR and LCVR CDRs selected from the group consisting of:
  a. CDR1, CDR2 and CDR3 amino acid sequences of SEQ ID NO:3 and CDR1, CDR2 and CDR3 amino acid sequences of SEQ ID NO:4;
  b. CDR1, CDR2 and CDR3 amino acid sequences of SEQ ID NO:5 and CDR1, CDR2 and CDR3 amino acid sequences of SEQ ID NO:6;
  c. CDR1, CDR2 and CDR3 amino acid sequences of SEQ ID NO:7 and CDR1, CDR2 and CDR3 amino acid sequences of SEQ ID NO:8;
  d. CDR1, CDR2 and CDR3 amino acid sequences of SEQ ID NO:9 and CDR1, CDR2 and CDR3 amino acid sequences of SEQ ID NO:10; and
  e. CDR1, CDR2 and CDR3 amino acid sequences of SEQ ID NO:13 and CDR1, CDR2 and CDR3 amino acid sequences of SEQ ID NO:14.

In a second preferred embodiment, the humanized anti-SIRPα antibody for use as defined hereinabove comprises an Fc region comprising the amino acid substitutions L234A and L235A, and HCVR and LCVR CDRs selected from the group consisting of:
  a. CDR1, CDR2 and CDR3 amino acid sequences of SEQ ID NO:5 and CDR1, CDR2 and CDR3 amino acid sequences of SEQ ID NO:6;
  b. CDR1, CDR2 and CDR3 amino acid sequences of SEQ ID NO:7 and CDR1, CDR2 and CDR3 amino acid sequences of SEQ ID NO:8; and
  c. CDR1, CDR2 and CDR3 amino acid sequences of SEQ ID NO:13 and CDR1, CDR2 and CDR3 amino acid sequences of SEQ ID NO:14.

In a third preferred embodiment, the humanized anti-SIRPα antibody for use as defined hereinabove comprises an Fc region comprising the amino acid substitutions L234A and L235A, and HCVR and LCVR CDRs selected from the group consisting of:
  a. CDR1, CDR2 and CDR3 amino acid sequences of SEQ ID NO:7 and CDR1, CDR2 and CDR3 amino acid sequences of SEQ ID NO:8; and
  b. CDR1, CDR2 and CDR3 amino acid sequences of SEQ ID NO:13 and CDR1, CDR2 and CDR3 amino acid sequences of SEQ ID NO:14.

In a fourth preferred embodiment, the humanized anti-SIRPα antibody for use as defined hereinabove comprises an Fc region comprising the amino acid substitutions L234A and L235A, and
  a. HCVR amino acid sequence of SEQ ID NO:30 and LCVR amino acid sequence of SEQ ID NO:31;
  b. HCVR amino acid sequence of SEQ ID NO:32 and LCVR amino acid sequence of SEQ ID NO:33;
  c. HCVR amino acid sequence of SEQ ID NO:34 and LCVR amino acid sequence of SEQ ID NO:8;
  d. HCVR amino acid sequence of SEQ ID NO:35 and LCVR amino acid sequence of SEQ ID NO:36;
  e. HCVR amino acid sequence of SEQ ID NO:35 and LCVR amino acid sequence of SEQ ID NO:37;
  f. HCVR amino acid sequence of SEQ ID NO:13 and LCVR amino acid sequence of SEQ ID NO:38; or
  g. HCVR amino acid sequence of SEQ ID NO:13 and LCVR amino acid sequence of SEQ ID NO:37.

In one preferred embodiment, the humanized anti-SIRPα antibody for use as defined hereinabove comprises an Fc region comprising the amino acid substitutions L234A and L235A, and HCVR amino acid sequence of SEQ ID NO:30 and LCVR amino acid sequence of SEQ ID NO:31. More preferably, the modified Fc IgG$_1$ region does not comprise either amino acid substitution N297A or N297G. Even more preferably, the modified Fc IgG$_1$ region does not comprise an amino acid substitution at position N297.

In another preferred embodiment, the humanized anti-SIRPα antibody for use as defined hereinabove comprises an Fc region comprising the amino acid substitutions L234A and L235A, and HCVR amino acid sequence of SEQ ID NO:32 and LCVR amino acid sequence of SEQ ID NO:33.

In yet another preferred embodiment, the humanized anti-SIRPα antibody for use as defined hereinabove comprises an Fc region comprising the amino acid substitutions L234A and L235A, and HCVR amino acid sequence of SEQ ID NO:34 and LCVR amino acid sequence of SEQ ID NO:8.

In yet another preferred embodiment, the humanized anti-SIRPα antibody for use as defined hereinabove comprises an Fc region comprising the amino acid substitutions L234A and L235A, and HCVR amino acid sequence of SEQ ID NO:35 and LCVR amino acid sequence of SEQ ID NO:36.

In yet another preferred embodiment, the humanized anti-SIRPα antibody for use as defined hereinabove comprises an Fc region comprising the amino acid substitutions L234A and L235A, and HCVR amino acid sequence of SEQ ID NO:35 and LCVR amino acid sequence of SEQ ID NO:37.

In yet another preferred embodiment, the humanized anti-SIRPα antibody for use as defined hereinabove comprises an Fc region comprising the amino acid substitutions L234A and L235A, and HCVR amino acid sequence of SEQ ID NO:13 and LCVR amino acid sequence of SEQ ID NO:38.

In yet another preferred embodiment, the humanized anti-SIRPα antibody for use as defined hereinabove comprises an Fc region comprising the amino acid substitutions L234A and L235A, and HCVR amino acid sequence of SEQ ID NO:13 and LCVR amino acid sequence of SEQ ID NO:37.

More preferably, the humanized anti-SIRPα antibodies as defined hereinabove for use as defined hereinabove comprising an Fc region comprising the amino acid substitutions L234A and L235A, the modified Fc $IgG_1$ region do not comprise either amino acid substitution N297A or N297G. Even more preferably, the modified Fc $IgG_1$ region does not comprise an amino acid substitution at position N297.

The anti-SIRPα antibodies comprising a modified Fc region that exhibits reduced binding to a human Fcα or Fcγ receptor, when compared to the same anti-SIRPα antibody comprising a wild-type Fc region as described hereinabove enhance the in vitro ADCC of a therapeutic antibody using neutrophils as effector cells from different donors homozygous for either $SIRPα_{BIT}$ or $SIRPα_1$. All of these antibodies increase the in vitro ADCC using neutrophils of most donors, the preferred antibodies even increase in vitro ADCC using neutrophils of all donors.

EXAMPLES

Immunization Protocol and Selection

Rabbits were repeatedly immunized with a mixture of peptides representing the extra cellular domain region of human (hu)$SIRPα_{BIT}$, human (hu)$SIRPα_1$ and cynomolgus (cy)SIRPα. Blood was collected at different time points and enriched with lymphocytes.

Single B-cells were deposited into single wells of microtiter plates. These B-cells were cultivated for several days in the presence of conditioned medium and feeder cells. During this time they produced and released monoclonal antibodies into the cultivation medium (B-cell supernatants). The supernatants of these single B-cells were analyzed for IgG production; subsequently the specific binding hu$SIRPα_{BIT}$ and hu$SIRPα_1$, to cySIRPα and to an anti-Fc antibody was determined. Suitable supernatants were those binding to both hu$SIRPα_{BIT}$ and hu$SIRPα_1$ and to cySIRPα. After a hit picking step binding to mouse (mu) SIRPα and to hu$SIRPβ_{1v1}$, hu$SIRPβ_{1v2}$ and huSIRPγ (as anti-targets) was measured. In addition, the binding to $SIRPα_{BIT}$ and $SIRPα_1$-over expressing CHO cells was determined. Binding to parental CHO cells was applied as a control assay.

Suitable B-cell lysates were selected for RNA isolation, reverse transcription and sequencing. The unique variable regions of antibody light and heavy chains were gene synthesized and cloned in front of the antibody constant region sequence (kappa LC SEQ ID NO:26 and human $IgG_1$ HC-LALA format SEQ ID NO:27), respectively.

HEK 293 cells were transiently transfected with the antibody sequence containing plasmids using an automated procedure on a Tecan Freedom Evo platform. Immunoglobulins were purified from the cell supernatant using affinity purification (Protein A) on a Dionex Ultimate 3000 HPLC system with a plate autosampler. The produced antibodies were tested in ELISA-type assays (ELISA: hu$SIRPα_1$, hu$SIRPα_{BIT}$, cySIRPα, muSIRPα, hu$SIRPβ_{1v1}$/$β_{1v2}$/γ; cell binding assays: hu$SIRPα_1$, hu$SIRPα_{BIT}$).

Transient Expression of Antibodies a) Preparation of cDNA Constructs and Expression Vectors The HCVR amino acid sequences of the antibodies were each joined at the N-terminus to a leader sequence (SEQ ID NO:28 for antibodies 1-9, 15, 16; SEQ ID NO:39 for antibodies 10-14), and at the C-terminus to the constant domain of a human $IgG_1$ HC LALA according to SEQ ID NO:27. The HCVR amino acid sequences of antibodies 12C4hu$IgG_1$LALA, 12C4hu$IgG_1$ or 29AM4-5hu$IgG_1$LALA were each joined at the N-terminus to a HAVT20 leader sequence (SEQ ID NO:29) and at the C-terminus to the constant domain of a human $IgG_1$ HC LALA according to SEQ ID NO:27 or a wild type human $IgG_1$ HC (SEQ ID NO:25). The resulting chimeric amino acid sequences were back-translated into a cDNA sequence codon-optimized for expression in human cells (*Homo sapiens*). Similarly, the chimeric cDNA sequence for the LC of the construct was obtained by joining the sequences of a leader sequence (SEQ ID NO:28 for antibodies 1-9, 12; SEQ ID NO:40 for antibodies 10, 11, 13-16, SEQ ID NO:29 for 12C4hu$IgG_1$LALA, 12C4hu$IgG_1$ and 29AM4-5hu$IgG_1$LALA) to the LCVR of antibodies 1-16, 12C4hu$IgG_1$LALA and 12C4hu$IgG_1$ and 29AM4-5hu$IgG_1$LALA at the N-terminus and at the C-terminus to a human $IgG_1$ κ light chain constant region (SEQ ID NO:26). The HCVR and LCVR sequences according to Table 1 were used.

TABLE 1

HCVR and LCVR sequences of the antibodies and reference antibodies

| Antibody | HCVR | LCVR |
|---|---|---|
| 1 | SEQ ID NO: 1 | SEQ ID NO: 2 |
| 2 | SEQ ID NO: 3 | SEQ ID NO: 4 |
| 3 | SEQ ID NO: 5 | SEQ ID NO: 6 |
| 4 | SEQ ID NO: 7 | SEQ ID NO: 8 |
| 5 | SEQ ID NO: 9 | SEQ ID NO: 10 |
| 6 | SEQ ID NO: 11 | SEQ ID NO: 12 |
| 7 | SEQ ID NO: 13 | SEQ ID NO: 14 |
| 8 | SEQ ID NO: 15 | SEQ ID NO: 16 |
| 9 | SEQ ID NO: 17 | SEQ ID NO: 18 |
| 29AM4-5hu$IgG_1$LALA | SEQ ID NO: 19 | SEQ ID NO: 20 |
| 12C4hu$IgG_1$LALA | SEQ ID NO: 21 | SEQ ID NO: 22 |
| 12C4hu$IgG_1$ | SEQ ID NO: 21 | SEQ ID NO: 22 |
| KWAR23 | SEQ ID NO: 23 | SEQ ID NO: 24 |
| 10 humanized | SEQ ID NO: 30 | SEQ ID NO: 31 |
| 11 humanized | SEQ ID NO: 32 | SEQ ID NO: 33 |
| 12 humanized | SEQ ID NO: 34 | SEQ ID NO: 8 |
| 13 humanized | SEQ ID NO: 35 | SEQ ID NO: 36 |
| 14 humanized | SEQ ID NO: 35 | SEQ ID NO: 37 |
| 15 humanized | SEQ ID NO: 13 | SEQ ID NO: 38 |
| 16 humanized | SEQ ID NO: 13 | SEQ ID NO: 37 | b) Vector Construction and Cloning Strategy

For expression of the antibody chains a mammalian expression vector was used, which contains a CMV:BGHpA expression cassette. The final vectors containing either the HC or the LC expression cassette (CMV:HC:BGHpA and CMV:LC-BGHpA, respectively) were transferred to and expanded in *E. coli* NEB 5-alpha cells. Large-scale production of the final expression vectors for transfection was performed using Maxi- or Megaprep kits (Qiagen).

c) Transient Expression in Mammalian Cells

Commercially available Expi293F cells (Thermo Fisher) were transfected with the expression vectors using the ExpiFectamine transfection agent according to the manufacturer's instructions as follows: 75×10$^7$ cells were seeded in 300 mL FortiCHO medium, 300 µg of the expression vector was combined with 800 µl of ExpiFectamine transfection agent and added to the cells. One day after transfection, 1.5 ml Enhancer 1 and 15 ml Enhancer 2 were added to the culture. Six days post transfection, the cell culture supernatant was harvested by centrifugation at 4,000 g for 15 min and filtering the clarified harvest over PES bottle filters/MF 75 filters (Nalgene).

Antibody Binding and Specificity

Experimental

ELISA assay: Solutions of huSIRPα$_1$, huSIRPα$_{BIT}$, huSIRPβ$_{1v1}$, huSIRPβ$_{1v2}$, huSIRPγ and cySIRPα in phosphate buffered saline (PBS) were each added to a multiple well black polystyrene plate for ELISA and allowed to adhere for 1 h at RT. Unbound protein was removed with three washing steps using standard washing buffer. Subsequently, blocking buffer was added to the wells. After 1 h incubation at RT, the wells were washed three times with standard washing buffer. The antibodies in buffer at various concentrations were added to the wells and incubated at RT for 1 h. Unbound antibodies were removed with three washing steps using standard washing buffer. Goat anti human IgG (Fab')$_2$:horse radish peroxidase (HRP) in buffer was added to the wells and incubated at RT for 1 h. 3,3',5,5'-Tetramethylbenzidine (TMB) was added and after sufficient colour development HC1 was added. Absorbance was read at 450 nm/620 nm.

Surface Plasmon Resonance (SPR) assay: Affinity analysis was performed by single cycle kinetics analysis on a Surface Plasmon Resonance apparatus (Biacore T200 system, GE Life Sciences) at 25° C. Biotinylated SIRP antigens were captured on the surface of a chip suitable for biotinylated molecules (Sensor Chip CAP, GE Life Sciences) by injecting 5 µg/ml of the SIRP antigen in running buffer (10 mM HEPES buffer at pH 7.4 with 150 mM NaCl, 3 mM EDTA and 0.005% v/v polyoxyethylene (20) sorbitan monolaurate (Surfactant P20) for 60 sec at 10 µL/min after injection of a streptavidin conjugate (20× diluted biotin CAPture reagent, GE Life Sciences) for 60 sec at 10 µl/min. Baseline stabilization was set at 1 min after which five increasing concentrations of an anti-SIRP antibody in running buffer (10 mM HEPES buffer at pH 7.4 with 150 mM NaCl 3 mM EDTA and 0.005% v/v polyoxyethylene (20) sorbitan monolaurate) were injected. For each step an association time of 150 sec was used, followed by a dissociation time of 1200 sec at the highest concentration only, all at a flow rate of 30 µL/min. Regeneration was performed with 6 M guanidine-HCl, 0.25 M NaOH solution (60 sec with flow rate of 30 µL/min). Double blank subtraction was performed on the observed sensorgrams using a non anti-SIRP (blank) immobilized reference flow channel and running buffer injection. Sensorgrams were fitted with a 1:1 Langmuir model for all tested anti-SIRP antibodies. The kinetic parameters ($k_a$, $k_d$ and $K_D$) were calculated using the Biacore T200 evaluation software (v3.1).

Flow Cytometry: U937 cells endogenously expressing human SIRPα$_{BIT}$ antigen and cells derived from a non-engineered subclone that has been screened and isolated from CHO-S Chinese hamster ovary cells (ExpiCHO-S) cells expressing human SIRPα$_1$, SIRPα$_{BIT}$ or cySIRPα antigen (100,000 cells/well in a 96-well plate) were washed three times with ice-cold FACS buffer (1×PBS (LONZA) containing 0.2% v/w BSA (Sigma-Aldrich, St. Louis, Mo.) and 0.02% v/w NaN$_3$ (Sigma-Aldrich), followed by the addition of a concentration range of each primary mAb (50 µL/well) diluted in ice-cold FACS buffer. After an incubation time of 30 min at 4° C., the cells were washed three times with ice-cold FACS buffer and 50 µL/well secondary mAb (AffiniPure F(ab')$_2$ fragment Goat-anti-human IgG-APC, 1:6,000 dilution, Jackson Immuno Research) was added. After 30 min at 4° C., cells were washed twice and resuspended in 150 µL FACS buffer. Fluorescence intensities were determined by flow cytometry (BD FACSVerse, Franklin Lakes, N.J.) and indicated as the median fluorescence intensity (MFI-Median) for U937 cells and ExpiCHO-S cells. Curves were fitted by nonlinear regression using the sigmoidal dose-response equation with variable slope (four parameters) in GraphPad Prism (version 7.02 for Windows, GraphPad, San Diego, Calif.). EC$_{50}$ values were calculated as the concentration in µg/mL that gives a response half way between bottom and top of the curve, when using a 4-parameter logistic fit.

Results

ELISA assay: The EC$_{50}$ values for binding to huSIRPα$_1$, huSIRPα$_{BIT}$, huSIRPβ$_1$, huSIRPβ$_{1v2}$, huSIRPγ, cySIRPα obtained with ELISA for antibodies 1-9 and reference antibodies are summarized in Table 2. All antibodies bind to huSIRPα$_1$ and to huSIRPα$_{BIT}$. Antibodies 29AM4-5huIgG$_1$LALA and 12C4huIgG$_1$LALA, bind to huSIRPβ$_{1v1}$, huSIRPβ$_{1v2}$, and huSIRPγ. The antibodies 2-6, 8 and 9 show a low affinity for huSIRPβ$_{1v1}$ and for huSIRPγ. Antibody 7 binds to huSIRPβ$_{1v1}$, but has low affinity for huSIRPβ$_{1v2}$ and huSIRPγ. Antibody 1 binds to huSIRPβ$_{1v2}$ and huSIRPγ.

TABLE 2

Specificity of the anti-SIRPα antibodies and reference antibodies

| Antibody | huSIRPα$_1$ EC$_{50}$ (ng/ml) | huSIRPα$_{BIT}$ EC$_{50}$ (ng/ml) | huSIRPβ$_{1v1}$ EC$_{50}$ (ng/ml) | huSIRPβ$_{1v2}$ EC$_{50}$ (ng/ml) | huSIRPγ EC$_{50}$ (ng/ml) | cySIRPα EC$_{50}$ (ng/ml) |
|---|---|---|---|---|---|---|
| 1 | 39 | 21 | 100,000 | 58 | 43 | 305 |
| 2 | 33 | 27 | 100,000 | 28 | 100,000 | 38 |
| 3 | 15 | 24 | 100,000 | 89 | 5,216 | 36 |
| 4 | 53 | 25 | 100,000 | 92 | 100,000 | 99 |
| 5 | 31 | 21 | 3,518 | 110 | 100,000 | 123 |
| 6 | 21 | 20 | 100,000 | 24 | 100,000 | 33 |
| 7 | 23 | 20 | 14 | 100,000 | 100,000 | 335 |
| 8 | 19 | 20 | 100,000 | 19 | 100,000 | 26 |
| 9 | 23 | 26 | 100,000 | 47 | 100,000 | 30 |
| 29AM4-5* | 9 | 9 | 13 | 17 | 34 | 11 |
| 12C4* | 7 | 5 | 8 | 6 | 6 | 5 |

*huIgG$_1$LALA

EC$_{50}$ values >100,000 have been adjusted to 100,000.

SPR assay: The $K_D$ values for binding to huSIRPα$_1$, huSIRPα$_{BIT}$ and huSIRPγ of antibodies 4, 7, 10-14 in comparison with reference antibodies KWAR23, huIgG$_1$ 12C4LALA and SE5A5 (purchased from a commercial supplier) are summarized in Table 3. Antibodies 4, 7, 10-14 bind to both huSIRPα$_1$ and huSIRPα$_{BIT}$, and do not bind to huSIRPγ. All reference antibodies do bind to huSIRPγ.

TABLE 3

SPR data ($K_D$ in M)

| Antibody | $K_D$ (huSIRPα$_{BIT}$) | $K_D$ (huSIRPα$_1$) | $K_D$ (huSIRPγ) |
|---|---|---|---|
| KWAR23 mouse IgG2a | <1.0E-11[1] | <1.0E-11 | <1.0E-11 |
| KWAR23 huIgG$_1$LALA | <1.0E-11[1] | 1.1E-11 | <1.0E-11 |
| 12C4huIgG$_1$LALA | 1.5E-11 | 8.7E-11 | 1.6E-11 |
| SE5A5 | 2.6E-9 | 2.2E-9 | 4.9E-8 |
| 4 | <1.0E-11 | 2.6E-11 | N[2] |
| 7 | <1.0E-11 | <1.0E-11 | N |
| 10 humanized | <1.0E-11 | 3.2E-9 | N |
| 11 humanized | 1.4E-10 | 4.1E-8 | N |
| 12 humanized | <1.0E-11 | 5.9E-11 | N |
| 13 humanized | 1.2E-11 | <1.0E-11 | N |
| 14 humanized | 8.9E-11 | <1.0E-11 | N |

[1]<1.0E-11: $K_D$ is outside the range which means high affinity
[2]N: No specific binding found Flow Cytometry assay: The binding of various antibodies to huSIRPα$_1$, huSIRPα$_{BIT}$, and/or cySIRPα expressed on cells was determined by flow cytometry. The binding is indicated in EC$_{50}$ values, which are shown in Table 4. Antibodies 2, 4, 5, 7, 8, 10-14 bind to huSIRPα$_1$, huSIRPα$_{BIT}$ and cySIRPα. Antibodies 2, 4, 5, 7, 8, 10-14 bind to cySIRPα in the low μg/mL range.

TABLE 4

Flow Cytometry data

| Antibody | U937 cells (SIRPα$_{BIT}$) EC$_{50}$ (μg/mL) | ExpiCHO-S (huSIRPα$_1$) EC$_{50}$ (μg/mL) | ExpiCHO-S (huSIRPα$_{BIT}$) EC$_{50}$ (μg/mL) | ExpiCHO-S (cySIRPα) EC$_{50}$ (μg/mL) |
|---|---|---|---|---|
| 1 | — | — | — | — |
| 2 | 0.14 | 0.19 | 0.27 | 0.16 |
| 3 | 0.22 | — | — | — |
| 4 | 0.12 | 0.41 | 0.23 | 0.18 |
| 5 | 0.16 | 0.27 | 0.22 | 0.26 |
| 6 | — | — | — | — |
| 7 | 0.17 | 0.23 | 0.21 | 0.07 |
| 8 | 0.12 | 0.22 | 0.18 | 0.15 |
| 9 | 0.11 | — | — | — |
| 29AM4-5 huIgG$_1$LALA | 0.25 | — | — | — |
| 12C4huIgG$_1$LALA | 0.19 | — | — | — |
| KWAR23 huIgG$_1$LALA | 0.09 | — | — | — |
| 10 | 0.17 | 0.38 | 0.2 | 0.27 |
| 11 | 0.13 | 1.05 | 0.3 | 0.32 |
| 12 | 0.2 | 0.1 | 0.46 | 0.17 |
| 13 | 0.14 | 0.36 | 0.23 | 0.44 |
| 14 | 0.22 | 0.37 | 0.29 | 0.38 |
| 15 | 0.16 | — | — | — |
| 16 | 0.23 | — | — | — |

— value not determined

Antibody Blocking of CD47-SIRPα Binding

Experimental

CHO cells transfected with either SIRPα$_1$ or SIRPα$_{BIT}$ or parental CHO cells as control were seeded in 20 μl cell medium in a well plate with clear bottom and incubated overnight. Antibodies 1-9, 29AM4-5huIgG$_1$LALA or 12C4huIgG$_1$LALA reference antibodies together with a mixture of His tag® CD47 and anti-His tag® fluorescent detection antibody were added to the wells and incubated for 2 h. After incubation, the cells were washed with cell wash buffer. Fluorescence was determined using a screening system (CellInsight®, Thermo Scientific®) and total fluorescence per cell was determined.

Results

Antibodies 29AM4-5huIgG$_1$LALA, 12C4huIgG$_1$LALA, 3 and 7 block binding of CD47 to both CHO cells expressing huSIRPα$_1$ and CHO cells expressing huSIRPα$_{BIT}$ completely, antibodies 1, 2, 4-6, 8 and 9 do neither block binding of CD47 to CHO cells expressing huSIRPα$_1$ nor to CHO cells expressing huSIRPα$_{BIT}$.

ADCC Assay

Neutrophils of donors homozygous for either SIRPα$_1$ or SIRPα$_{BIT}$ were isolated and cultured according to the method in Chao et al. *PNAS* 2011, 108(45), 18342-18347. ADCC was determined using the $^{51}$Cr release assay or the non-radioactive Europium TDA (EuTDA) cytotoxicity assay (DELFIA, PerkinElmer). SKBR3 cells were used as target cells and labelled with 100 μCi $^{51}$Cr (Perkin-Elmer) for 90 min at 37° C., or with bis (acetoxymethyl) 2,2':6',2"-terpyridine-6,6"-dicarboxylate) (BATDA reagent Delfia), for 5 min at 37° C. After 2 washes with PBS, 5×10$^3$ target cells per well were incubated in IMDM culture medium supplemented with 10% (v/v) foetal calf serum (FCS) for 4 hours at 37° C. and 5% CO$_2$ in a 96-well U-bottom plate together with neutrophils in an effector to target cell ratio of 50:1 in the presence of the appropriate antibodies. After the incubation, supernatant was harvested and analyzed for radioactivity in a gamma counter (Wallac) or was added to europium solution (DELFIA, PerkinElmer) and the europium 2,2':6',2"-terpyridine-6,6"-dicarboxylic acid (EuTDA) fluorescence was determined using a spectrofluorometer (Envision, PerkinElmer). The percentage of cytotoxicity was calculated as [(experimental release−spontaneous release)/(total release−spontaneous release)]×100%. All conditions were measured in duplicate and/or triplicate.

ADCC data 12C4huIgG$_1$LALA Versus 12C4IgG$_1$

FIG. 1 shows the results of the ADCC assay as cytotoxicity in %. The % cytotoxicity measured on SKBR3 cells using neutrophils as effector cells and trastuzumab alone is less than the % cytotoxicity of trastuzumab in combination with the murine 12C4 antibody (mu12C4). Trastuzumab in combination with an antibody wherein 12C4 variable regions are grafted onto a human IgG$_1$ constant region (12C4huIgG$_1$) shows similar % cytotoxicity as compared to trastuzumab alone at low concentrations of 12C4huIgG$_1$. At higher concentrations 12C4huIgG$_1$, a decrease in % cytotoxicity is observed. Trastuzumab in combination with an antibody wherein 12C4 variable regions are grafted onto a human IgG$_1$ constant region comprising amino acid substitutions L234A and L235A (12C4huIgG$_1$LALA) shows increased % cytotoxicity compared to the % cytotoxicity of trastuzumab alone, and increased % cytotoxicity compared to the combination of 12C4huIgG$_1$ and trastuzumab.

ADCC Data

Figure 2:
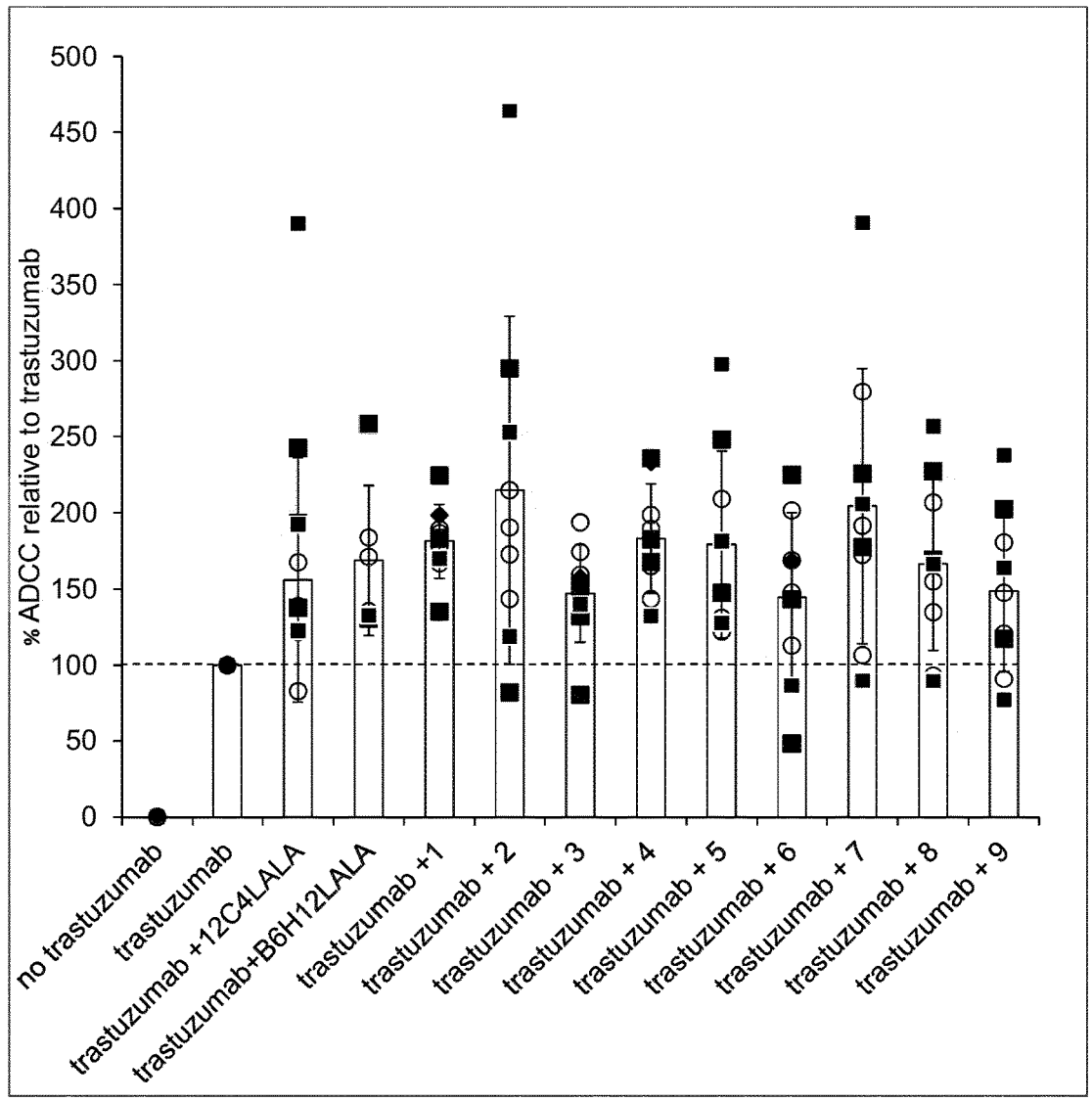
FIG. 2. Comparison of % ADCC relative to trastuzumab (set to 100%) of trastuzumab in combination with the anti-SIRPα antibodies 1-9 having a human IgG$_1$ constant region comprising the amino acid substitutions L234A and L235A, anti-SIRPα antibody 12C4huIgG$_1$LALA (12C4LALA) and anti-CD47 antibody B6H12huIgG$_1$LALA (B6H12LALA) on SKBR3 cells. Filled squares, (■), are the values measured with neutrophils of donors having the SIRPα$_{BIT}$ variant, open circles, (○), are the values measured with neutrophils of donors having the SIRPα$_1$ variant. Columns are the average of all donors; error bars represent the standard deviation.

FIG. 2 compares the % ADCC by human neutrophils relative to trastuzumab (set to 100%) in the presence of antibody 1-9 having a human IgG$_1$ constant region comprising amino acid substitutions L234A and L235A (LALA) in combination with trastuzumab in comparison with 12C4huIgG$_1$LALA. B6H12IgG$_1$LALA, having the VR of a murine anti-CD47 antibody and a human IgG$_1$ constant region comprising amino acid substitutions L234A and L235A, and vehicle (no trastuzumab) were used as positive and negative control, respectively. Filled squares, (■), are the values measured with neutrophils of donors having the SIRPα$_{BIT}$ variant (homozygous for SIRPα$_{BIT}$), open circles (○) are the values measured with neutrophils of donors having the SIRPα$_1$ variant (homozygous for SIRPα$_1$). For all antibodies the average ADCC was increased in comparison to trastuzumab alone. For antibodies 1, 2, 4, 5, 7 and 8 the average ADCC increase was enhanced even more than the 12C4huIgG$_1$LALA-induced ADCC increase. When the ADCC increase per donor per antibody is compared, antibodies 1, 3-6, 8 and 9 show less variation in % increase in ADCC than 12C4huIgG$_1$LALA.

Figure 3:
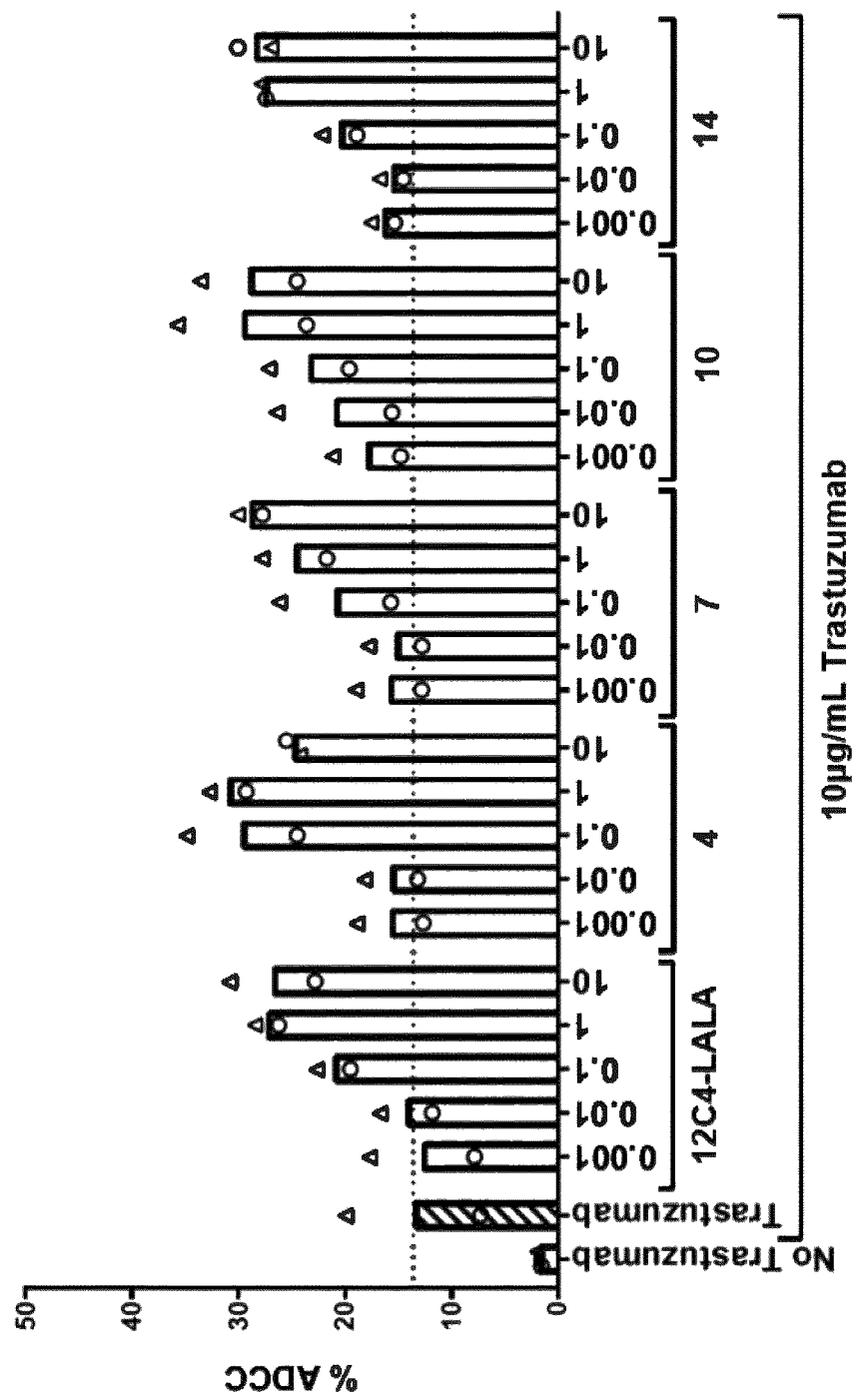
FIG. 3. Comparison of % ADCC relative to trastuzumab alone and trastuzumab in combination with the anti-SIRPα antibodies 4, 7, 10, 14 in various concentrations (dose response curves) having a human IgG$_1$ constant region comprising the amino acid substitutions L234A and L235A, and anti-SIRPα antibody 12C4huIgG$_1$LALA (12C4LALA) on SKBR3 cells. Neutrophils of two donors (Δ, ○) having the SIRPα$_{BIT}$ variant. Columns are the average of the two donors.

FIG. 3 compares the % ADCC by human neutrophils in the presence of various concentrations of chimeric antibodies 4 and 7 and humanized antibodies 10 and 14 having a human IgG$_1$ constant region comprising amino acid substitutions L234A and L235A (LALA) in combination with trastuzumab in comparison with trastuzumab alone and trastuzumab in combination with various concentrations of 12C4huIgG$_1$LALA. Neutrophils of two donors homozygous for SIRPα$_{BIT}$ were used. Even at low concentrations antibodies 4, 7, 10 and 14 increase ADCC. The ADCC increase is concentration dependent.

Figure 4:
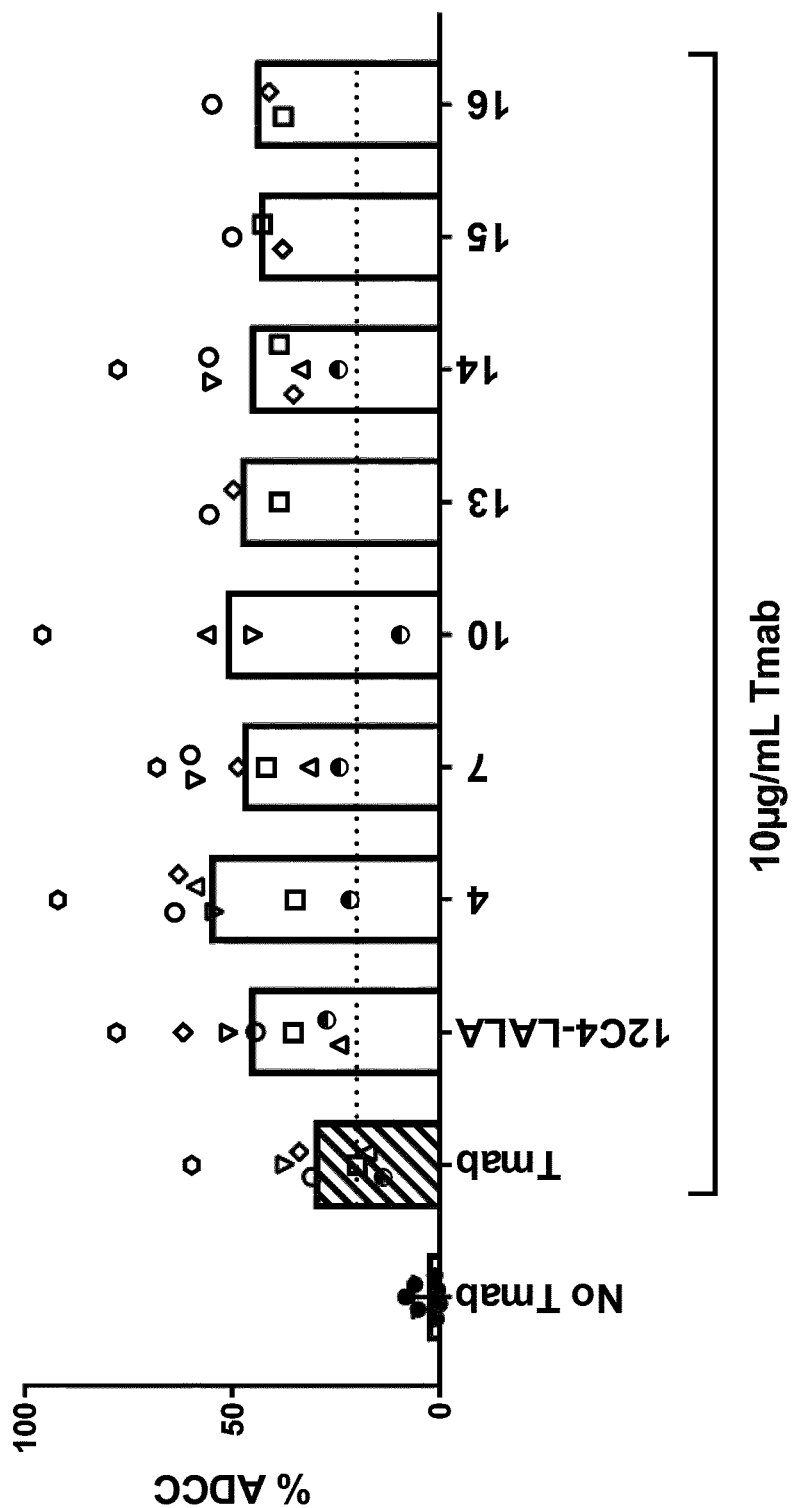
FIG. 4. Comparison of % ADCC relative to trastuzumab alone and trastuzumab in combination with the anti-SIRPα antibodies 4, 7, 10, 13, 14, 15 and 16 having a human IgG1 constant region comprising the amino acid substitutions L234A and L235A, and anti-SIRPα antibody 12C4huIgG1LALA (12C4LALA) on SKBR3 cells. Neutrophils of donors having the SIRPα$_{BIT}$ variant (Δ, ◯, ▽, ◇), having the SIRPα$_1$ variant (○, ●) and neutrophils of a donor which variant was not determined (□) were used. Columns are the average of the donors.

FIG. 4 compares the % ADCC by human neutrophils in the presence of antibodies 4, 7, 10, 13, 14, 15 and 16 in combination with trastuzumab (Tmab) in comparison with the % ADCC trastuzumab alone and 12C4huIgG$_1$LALA. All antibodies increase the ADCC in comparison with trastuzumab alone. The ADCC increase by neutrophils of most donors in the presence of antibodies 4, 7, 10, 13, 14, 15 and 16 in combination with trastuzumab is similar or increased in comparison with 12C4huIgG$_1$LALA in combination with trastuzumab.

```
Sequence listings with underlined CDR1, CDR2 and CDR3 amino
acid sequences in heavy chain (HC) and light chain (LC)
variable region (VR) amino acid sequences
(determined using the method of Kabat)
(HC VR 1)
                                                      SEQ ID NO: 1
    1 QSVEESGGRL VTPGTPLTLT CTVSGIDLSS YAMSWVRQAP GKGLEWIGII

51 SSGGITYYAS WAKGRFTISK TSTTVDLKIP SPTTEDTATY FCARSLWAAS

101 NYYMALWGPG TLVTVSS (LC VR 1)
                                                      SEQ ID NO: 2
    1 AIKMTQTPAS VSAAVGGTVS INCQASEDIE SYLAWYQQKP GQPPKLLIYR

51 ASTLASGVSS RFKGSGSGTQ FTLTISDLES ADAATYYCLG DYYSSSGDTG

101 AFGGGTEVVV K (HC VR 2)
                                                      SEQ ID NO: 3
    1 QSVEESGGRL VTPGTPLTLT CTVSGFSLSN YAMHWVRQAP GKGLEWIGII

51 YTGGATSYAT WAKGQFTISK TSTTVDLKIT SPTTEDTATY FCARGDRDGY

101 AYFNIWGPGT LVTVSL (LC VR 2)
                                                      SEQ ID NO: 4
    1 QIVMTQTPFS VSAVVGGTVT IKCQASHNIG SWLAWYQQKP GQRPKLLIYD

51 ASTLASGVSS RFKGSGSGTE FTLTISGVES ADAATYYCQQ GYGISYVHNV

101 FGGGTEVVVK
```

-continued (HC VR 3)
```
                                                      SEQ ID NO: 5
  1 QSVEESGGRL VTPGTPLTLA CTVSGFSLIS YYISWVRQAP EKGLEYIGII

51 NIGGGASYAS WAKGRFTISK TSTTVDLKIT SPTPEDTATY FCAMSYGMDT

101 GAFNIWGPGT LVTVSL
```

(LC VR 3)
```
                                                      SEQ ID NO: 6
  1 AQVLTQTPAS VSAAVGGTVT ISCQSSESVY KNNFLSWYQQ KPGKPPKLLI

51 YGASTLASGV PSRFKGSGSG TQFTLTISDL ESDDAATYFC QGGYRTDIYP

101 FGGGTEVVVK
```

(HC VR 4)
```
                                                      SEQ ID NO: 7
  1 QSVEESGGRL GTPGTPLTLT CTVSGFSLSS YVMGWFRQAP GKGLEYIGII

51 SSSGSPYYAS WVNGRFTISK TSTTMDLKMN SPTTEDTATY FCARVGPLGV

101 DYFNIWGPGT LVTVSL
```

(LC VR 4)
```
                                                      SEQ ID NO: 8
  1 DIVMTQTPSS VEAAVGGTVT IKCQAGQSIN SYLAWYQQKP GQRPKLLIYY

51 ASTLESGVPS RFKGSGSGTD YTLTISDLES ADAATYYCQS WHYISRSYAF

101 GGGTEVVVK
```

(HC VR 5)
```
                                                      SEQ ID NO: 9
  1 QSVEESGGRL VTPGTPLTLT CTVSGFSLSS YVMGWFRQAA GKGLEYIGYI

51 NADGSPYYAT WVNGRFTISK TPTTMDLKIN SPTTEDTATY FCARVGPLGV

101 DYFNIWGPGT LVTVSL
```

(LC VR 5)
```
                                                      SEQ ID NO: 10
  1 DIVMTQTPAS VEAAVGGTVT IKCQASQSIN RYLTWYQQKP GQRPKLLIYY

51 ASTLESGVPS RFEGSGSGTD YTLTISDLES ADAATYYCQS YYYISRTYAF

101 GGGTEV VVK
```

(HC VR 6)
```
                                                      SEQ ID NO: 11
  1 QSVEESGGRL VTPGTPLTLT CTVSGIDLSS YTMTWVRQAP GKGLEWIGII

51 YAGGSTAYAS WAKGRFTISK TSTTVDLKIT SPTTEDTATY FCARSSSDGY

101 DYFNIWGPGT LVTVS L
```

(LC VR 6)
```
                                                      SEQ ID NO: 12
  1 GVVMTQTPSS VSAAVGGTVT INCQASQSIG SWLAWYQQKP GQPPKLLIYQ

51 ASKLASGVPS RFSGRGSGTH FTLTISDVQS DDAATYYCQQ TVTAASNVDNA

101 FGGGTEVVVK
```

(HC VR 7)
```
                                                      SEQ ID NO: 13
  1 RSVEESGGRL VTPGTPLTLT CTVSGFSLSS HGISWVRQAP GKGLEYIGTI

51 GTGVITYFAS WAKGRFTGSK TSTTVDLKIT SPTTEDTATY FCARGSAWND

101 PFDPWGPGTL VTVSS
```

(LC VR 7)
```
                                                      SEQ ID NO: 14
  1 ALVMTQTPAS VSAAVGGTVT TKCQASQSVY GNNDLAWYQH KPGQPPKLLI

51 YLASTLATGV PSRFSGSGSG TQFTLTITGV QSDDAATYYC LGGGDDEADN

101 VFGGGTEVVV K
```

-continued (HC VR 8)
SEQ ID NO: 15
  1 QSLEESGGRL VTPGTPLTLT CTASGVDLSN YAMGWVRQAP GKGLEWIGII

51 YAGGSTSYAT WAKGRFTISK TSTTMDLKMT SPTTEDTATY FCARHRSDGY

101 DYFHLWGPGT LVTVSL (LC VR 8)
SEQ ID NO: 16
  1 AIDMTQTPAS VSEPVGGTVT IKCQASQSIS SWLAWYQQKP GQRPKLLIYD

51 ASKLASGVPS RFSGSGSGTE FTLTISGVQS DDAAAYYCQQ GYAVSYVENI

101 FGGGTEVVVK (HC VR 9)
SEQ ID NO: 17
  1 QSMEESGGRL VTPGTPLTLT CTASGFSLSN YGVSWVRQAP GKGLEWIGII

51 YGGSDITAYA SWAKGRFTIS KTSTTVDLTI TSPTTEDTAT YFCAKSYTNG

101 MDYYNIWGPG TLVTVSL (LC VR 9)
SEQ ID NO: 18
  1 AFDLTQTPSS VEAPVGGTVI IKCQASQSIS SYLAWYQQKP GQPPKLLIYS

51 ASTLASGVSS RFKGSGSETQ FPLTISDLES ADAATYYCQS YYGSRSNVFG

101 GGTEVVVK (HC VR 29AM4-5)
SEQ ID NO: 19
  1 EVQLVESGGG LVQPGGSLRL SCAASGFNIS YYFIHWVRQA PGKGLEWVAS

51 VYSSFGYTYY ADSVKGRFTI SADTSKNTAY LQMNSLRAED TAVYYCARFT

101 FPGLFDGFFG AYLGSLDYWG QGTLVTVSS (LC VR 29AM4-5)
SEQ ID NO: 20
  1 DIQMTQSPSS LSASVGDRVT ITCRASQSVS SAVAWYQQKP GKAPKLLIYS

51 ASSLYSGVPS RFSGSRSGTD FTLTISSLQP EDFATYYCQQ AVNWVGALVT

101 FGQGTKVEIK (HC VR 12C4)
SEQ ID NO: 21
  1 EVKLEESGGG LMQPGGSMKL SCVASGFTFS NYWMNWVRQS PEKGLEWVAE

51 IRLKSNNYAT HYAESVKGRF TISRDDSKSS VYLQMNNLRA EDTGIYYCIR

101 DYDYDAYFDY WGQGTTLTVS S (LC VR 12C4)
SEQ ID NO: 22
  1 DIVLTQSPAS LAVSLGQRAT ISCRASKSVS TSGYNYMYWY QQKPGQPPKL

51 LIYLASNLES GVPARFSGSG SGTDFTLNIH PVEEEDAATY YCQHSGELPY

101 TFGGGTKLEI K (HC VR KWAR23)
SEQ ID NO: 23
  1 EVQLQQSGAE LVKPGASVKL SCTASGFNIK DYYIHWVQQR TEQGLEWIGR

51 IDPEDGETKY APKFQDKATI TADTSSNTAY LHLSSLTSED TAVYYCARWG

101 AYWGQGTLVT VSS (LC VR KWAR23)
SEQ ID NO: 24
  1 QIVLTQSPAI MSASPGEKVT LTCSASSSVS SSYLYWYQQK PGSSPKLWIY

51 STSNLASGVP ARFSGSGSGT SYSLTISSME AEDAASYFCH QWSSYPRTFG

101 AGTKLELK (human IgG₁ antibody HC constant region)
SEQ ID NO: 25
```
  1 ASTKGPSVFP LAPSSKSTSG GTAALGCLVK DYFPEPVTVS WNSGALTSGV
 51 HTFPAVLQSS GLYSLSSVVT VPSSSLGTQT YICNVNHKPS NTKVDKKVEP
101 KSCDKTHTCP PCPAPELLGG PSVFLFPPKP KDTLMISRTP EVTCVVVDVS
151 HEDPEVKFNW YVDGVEVHNA KTKPREEQYN STYRVVSVLT VLHQDWLNGK
201 EYKCKVSNKA LPAPIEKTIS KAKGQPREPQ VYTLPPSRDE LTKNQVSLTC
251 LVKGFYPSDI AVEWESNGQP ENNYKTTPPV LDSDGSFFLY SKLTVDKSRW
301 QQGNVFSCSV MHEALHNHYT QKSLSLSPGK
```

(human IgG₁ antibody LC κ constant region)
SEQ ID NO: 26
```
  1 RTVAAPSVFI FPPSDEQLKS GTASVVCLLN NFYPREAKVQ WKVDNALQSG
 51 NSQESVTEQD SKDSTYSLSS TLTLSKADYE KHKVYACEVT HQGLSSPVTK
101 SFNRGEC
```

(human IgG₁ antibody HC constant region LALA mutant (mutations underlined))
SEQ ID NO: 27
```
  1 ASTKGPSVFP LAPSSKSTSG GTAALGCLVK DYFPEPVTVS WNSGALTSGV
 51 HTFPAVLQSS GLYSLSSVVT VPSSSLGTQT YICNVNHKPS NTKVDKKVEP
101 KSCDKTHTCP PCPAPEAAGG PSVFLFPPKP KDTLMISRTP EVTCVVVDVS
151 HEDPEVKFNW YVDGVEVHNA KTKPREEQYN STYRVVSVLT VLHQDWLNGK
201 EYKCKVSNKA LPAPIEKTIS KAKGQPREPQ VYTLPPSRDE LTKNQVSLTC
251 LVKGFYPSDI AVEWESNGQP ENNYKTTPPV LDSDGSFFLY SKLTVDKSRW
301 QQGNVFSCSV MHEALHNHYT QKSLSLSPGK
```

(leader sequence HC 1-9, 15 + 16, LC 1-9 + 12)
SEQ ID NO: 28
```
  1 MGWSCIILFL VATATGVHS
```

(HAVT20 leader sequence)
SEQ ID NO: 29
```
  1 MACPGFLWAL VISTCLEFSMA
```

(HC VR 10)
SEQ ID NO: 30
```
  1 KVEESGGGLV QPGGSLRLSC AASGFSLSSY VMGWVRQAPG KGLEWVSIIS
 51 SSGSPYYASW VNGRFTISKD NSEGMVYLQM NSLRAEDTAV YYCARVGPLG
101 VDYFNIWGQG TTVTVSS
```

(LC VR 10)
SEQ ID NO: 31
```
  1 DIVMTQSPDS LAVSLGERAT INCQAGQSIN SYLAWYQQKP GQPPKLLIYY
 51 ASTLESGVPD RFSGSGSGTD FTLTISSLQA EDVAVYYCQS WHYISRSYAF
101 GGGTKLEIK
```

(HC VR 11)
SEQ ID NO: 32
```
  1 EVKVEESGGG LVQPGGSLRL SCAASGFSLS SYVMGWVRQA PGKGLEWVSI
 51 ISSSGSPYYA SWVNGRFTIS KTSTTMDLQM NSLRAEDTAV YYCARVGPLG
101 VDYFNIWGQG TTVTVSS
```

(LC VR 11)
SEQ ID NO: 33
```
  1 DIQMTQSPSS LSASVGDRVT ITCQAGQSIN SYLAWYQQKP GKVPKLLIYY
 51 ASTLESGVPS RFSGSGSGTD FTLTISSLQP EDVATYYCQS WHYISRSYAF
101 GQGTKVEIK
```

-continued (HC VR 12)
SEQ ID NO: 34

1 VQLVESGGRL VQPGTPLTLS CTVSGFSLSS YVMGWFRQAP GKGLEYIGII

51 SSSGSPYYAS WVNGRFTISK TSTTMDLKMN SLRSEDTATY FCARVGPLGV

101 DYFNIWGPGT LVTVSS (HC VR 13 + 14)
SEQ ID NO: 35

1 RQLVESGGGL VQPGGSLRLS CTASGFSLSS HGISWVRQAP GKGLEYIGTI

51 GTGVITYFAS WAKGRFTGSK TSSTAYMELS SLRSEDTAVY FCARGSAWND

101 PFDPWGQGTL VTVSS (LC VR 13)
SEQ ID NO: 36

1 AIQMTQSPSS LSASVGDRVT ITCQASQSVY GNNDLAWYQQ KPGKAPKLLI

51 YLASTLATGV PSRFSGSGSG TDFTLTISSL QPEDFATYYC LGGGDDEADN

101 VFGGGTKVEI K (LC VR 14 + 16)
SEQ ID NO: 37

1 DIEMTQSPSS VSASVGDRVT LTCQASQSVY GNNDLAWYQQ KPGQAPKLLI

51 YLASTLATGV PSRFSGSGSG TDFTLTISSL QPEDFATYYC LGGGDDEADN

101 VFGGGTKVEI K (LC VR 15)
SEQ ID NO: 38

1 ELVMTQSPSS LSASVGDRVT ITCQASQSVY GNNDLAWYQQ KPGEAPKLLI

51 YLASTLATGV PSRFSGSGSG TDFTLTISGL QSEDFATYYC LGGGDDEADN

101 VFGQGTKVEI K (leader sequence heavy chains 10-14)
SEQ ID NO: 39

1 MGWTLVFLFL LSVTAGVHS (leader sequence light chains 10, 11, 13-16)
SEQ ID NO: 40

1 MVSSAQFLGL LLLCFQGTRC

---

The invention claimed is:

1. An anti-SIRPα antibody or an antigen-binding fragment thereof comprising heavy chain (HC) and light chain (LC) variable region (VR) complementarity determining regions (CDRs) selected from the group consisting of:
   (a) CDR1, CDR2 and CDR3 amino acid sequences of SEQ ID NO:3 and CDR1, CDR2 and CDR3 amino acid sequences of SEQ ID NO:4;
   (b) CDR1, CDR2 and CDR3 amino acid sequences of SEQ ID NO:5 and CDR1, CDR2 and CDR3 amino acid sequences of SEQ ID NO:6;
   (c) CDR1, CDR2 and CDR3 amino acid sequences of SEQ ID NO:7 and CDR1, CDR2 and CDR3 amino acid sequences of SEQ ID NO:8;
   (d) CDR1, CDR2 and CDR3 amino acid sequences of SEQ ID NO:9 and CDR1, CDR2 and CDR3 amino acid sequences of SEQ ID NO:10;
   (e) CDR1, CDR2 and CDR3 amino acid sequences of SEQ ID NO:11 and CDR1, CDR2 and CDR3 amino acid sequences of SEQ ID NO:12;
   (f) CDR1, CDR2 and CDR3 amino acid sequences of SEQ ID NO:13 and CDR1, CDR2 and CDR3 amino acid sequences of SEQ ID NO:14;
   (g) CDR1, CDR2 and CDR3 amino acid sequences of SEQ ID NO:15 and CDR1, CDR2 and CDR3 amino acid sequences of SEQ ID NO:16; and
   (h) CDR1, CDR2 and CDR3 amino acid sequences of SEQ ID NO:17 and CDR1, CDR2 and CDR3 amino acid sequences of SEQ ID NO:18; and
   wherein the CDRs are determined according to Kabat numbering.

2. The antibody according to claim 1, which is chimeric, humanized or human.

3. The antibody according to claim 2, comprising HCVR and LCVR CDRs selected from the group consisting of:
   (a) CDR1, CDR2 and CDR3 amino acid sequences of SEQ ID NO:7 and CDR1, CDR2 and CDR3 amino acid sequences of SEQ ID NO:8; and
   (b) CDR1, CDR2 and CDR3 amino acid sequences of SEQ ID NO:13 and CDR1, CDR2 and CDR3 amino acid sequences of SEQ ID NO:14; and
   wherein the antibody is humanized.

4. The antibody according to claim 3, comprising:
   (a) CDR1, CDR2 and CDR3 amino acid sequences of SEQ ID NO:7, CDR1, CDR2 and CDR3 amino acid sequences of SEQ ID NO:8, HCVR amino acid sequence of SEQ ID NO:30 and LCVR amino acid sequence of SEQ ID NO:31;
   (b) CDR1, CDR2 and CDR3 amino acid sequences of SEQ ID NO:7, CDR1, CDR2 and CDR3 amino acid sequences of SEQ ID NO:8, HCVR amino acid sequence of SEQ ID NO:32 and LCVR amino acid sequence of SEQ ID NO:33;
   (c) CDR1, CDR2 and CDR3 amino acid sequences of SEQ ID NO:7, CDR1, CDR2 and CDR3 amino acid sequences of SEQ ID NO:8, HCVR amino acid sequence of SEQ ID NO:34 and LCVR amino acid sequence of SEQ ID NO:8;
   (d) CDR1, CDR2 and CDR3 amino acid sequences of SEQ ID NO:13, CDR1, CDR2 and CDR3 amino acid sequences of SEQ ID NO:14, HCVR amino acid sequence of SEQ ID NO:35 and LCVR amino acid sequence of SEQ ID NO:36;
   (e) CDR1, CDR2 and CDR3 amino acid sequences of SEQ ID NO:13, CDR1, CDR2 and CDR3 amino acid sequences of SEQ ID NO:14 and HCVR amino acid sequence of SEQ ID NO:35 and LCVR amino acid sequence of SEQ ID NO:37;
   (f) HCVR amino acid sequence of SEQ ID NO:13, CDR1, CDR2 and CDR3 amino acid sequences of SEQ ID NO:14 and LCVR amino acid sequence of SEQ ID NO:38; or
   (g) HCVR amino acid sequence of SEQ ID NO:13, CDR1, CDR2 and CDR3 amino acid sequences of SEQ ID NO:14 and LCVR amino acid sequence of SEQ ID NO:37.

5. The anti-SIRPα antibody according to claim 1, comprising a modified Fc region that exhibits reduced binding to a human Fcα or Fcγ receptor compared to the same anti-SIRPα antibody comprising a wild-type Fc region.

6. The anti-SIRPα antibody according to claim 1, comprising a modified human $IgG_1$ Fc region comprising one or more amino acid substitutions at one or more positions selected from the group consisting of L234, L235, G237, D265, D270, N297, A327, P328, and P329 according to Eu numbering.

7. The anti-SIRPα antibody according to claim 6, comprising the amino acid substitutions L234A and L235A; L234E and L235A; L234A, L235A and P329A; or L234A, L235A and P329G.

8. The anti-SIRPα antibody according to claim 7, comprising the amino acid substitutions L234A and L235A; or L234E and L235A.

9. A pharmaceutical composition comprising the anti-SIRPα antibody according to claim 1 and one or more pharmaceutically acceptable excipients.

10. A pharmaceutical composition comprising the anti-SIRPα antibody according to claim 3 and one or more pharmaceutically acceptable excipients.

* * * * *

SEQUENCE LISTING

<160> NUMBER OF SEQ ID NOS: 40

<210> SEQ ID NO 1
<211> LENGTH: 117
<212> TYPE: PRT
<213> ORGANISM: Artificial Sequence
<220> FEATURE:
<223> OTHER INFORMATION: SEQ ID NO:1 (HC VR 1)

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Ser Gly Gly Ile Thr Tyr Tyr Ala Ser Trp Ala Lys Gly
    50                  55                  60

Arg Phe Thr Ile Ser Lys Thr Ser Thr Val Asp Leu Lys Ile Pro
65                  70                  75                  80

```
Ser Pro Thr Thr Glu Asp Thr Ala Thr Tyr Phe Cys Ala Arg Ser Leu
            85                  90                  95

Trp Ala Ala Ser Asn Tyr Tyr Met Ala Leu Trp Gly Pro Gly Thr Leu
            100                 105                 110

Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: SEQ ID NO:2 (LC VR 1)

<400> SEQUENCE: 2

Ala Ile Lys Met Thr Gln Thr Pro Ala Ser Val Ser Ala Ala Val Gly
1               5                   10                  15

Gly Thr Val Ser Ile Asn Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Ser
65                  70                  75                  80

Ala Asp Ala Ala Thr Tyr Tyr Cys Leu Gly Asp Tyr Tyr Ser Ser Ser
                85                  90                  95

Gly Asp Thr Gly Ala Phe Gly Gly Gly Thr Glu Val Val Val Lys
            100                 105                 110

<210> SEQ ID NO 3
<211> LENGTH: 116
<212> TYPE: PRT
<213> ORGANISM: Artificial Sequence
<220> FEATURE:
<223> OTHER INFORMATION: SEQ ID NO:3 (HC VR 2)

<400> SEQUENCE: 3

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met His Trp Val Arg Gln Ala Pro Gly Lys Gly Leu Glu Trp Ile Gly
        35                  40                  45

Ile Ile Tyr Thr Gly Gly Ala Thr Ser Tyr Ala Thr Trp Ala Lys Gly
    50                  55                  60

Gln Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asp
                85                  90                  95

Arg Asp Gly Tyr Ala Tyr Phe Asn Ile Trp Gly Pro Gly Thr Leu Val
            100                 105                 110

Thr Val Ser Leu
        115

<210> SEQ ID NO 4
<211> LENGTH: 110
<212> TYPE: PRT
<213> ORGANISM: Artificial Sequence
```

<220> FEATURE:
<223> OTHER INFORMATION: SEQ ID NO:4 (LC VR 2)

<400> SEQUENCE: 4

```
Gln Ile Val Met Thr Gln Thr Pro Phe Ser Val Ser Ala Val Val Gly
1               5                   10                  15

Gly Thr Val Thr Ile Lys Cys Gln Ala Ser His Asn Ile Gly Ser Trp
            20                  25                  30

Leu Ala Trp Tyr Gln Gln Lys Pro Gly Gln Arg Pro Lys Leu Leu Ile
        35                  40                  45

Tyr Asp Ala Ser Thr Leu Ala Ser Gly Val Ser Ser Arg Phe Lys Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Tyr Gly Ile Ser Tyr
                85                  90                  95

Val His Asn Val Phe Gly Gly Gly Thr Glu Val Val Val Lys
            100                 105                 110
```

<210> SEQ ID NO 5
<211> LENGTH: 116
<212> TYPE: PRT
<213> ORGANISM: Artificial Sequence
<220> FEATURE:
<223> OTHER INFORMATION: SEQ ID NO:5 (HC VR 3)

<400> SEQUENCE: 5

```
Gln Ser Val Glu Glu Ser Gly Gly Arg Leu Val Thr Pro Gly Thr Pro
1               5                   10                  15

Leu Thr Leu Ala Cys Thr Val Ser Gly Phe Ser Leu Ile Ser Tyr Tyr
            20                  25                  30

Ile Ser Trp Val Arg Gln Ala Pro Glu Lys Gly Leu Glu Tyr Ile Gly
        35                  40                  45

Ile Ile Asn Ile Gly Gly Gly Ala Ser Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Pro Glu Asp Thr Ala Thr Tyr Phe Cys Ala Met Ser Tyr
                85                  90                  95

Gly Met Asp Thr Gly Ala Phe Asn Ile Trp Gly Pro Gly Thr Leu Val
            100                 105                 110

Thr Val Ser Leu
        115
```

<210> SEQ ID NO 6
<211> LENGTH: 110
<212> TYPE: PRT
<213> ORGANISM: Artificial Sequence
<220> FEATURE:
<223> OTHER INFORMATION: SEQ ID NO:6 (LC VR 3)

<400> SEQUENCE: 6

```
Ala Gln Val Leu Thr Gln Thr Pro Ala Ser Val Ser Ala Ala Val Gly
1               5                   10                  15

Gly Thr Val Thr Ile Ser Cys Gln Ser Ser Glu Ser Val Tyr Lys Asn
            20                  25                  30

Asn Phe Leu Ser Trp Tyr Gln Gln Lys Pro Gly Lys Pro Pro Lys Leu
        35                  40                  45
```

```
Leu Ile Tyr Gly Ala Ser Thr Leu Ala Ser Gly Val Pro Ser Arg Phe
 50                  55                  60

Lys Gly Ser Gly Ser Gly Thr Gln Phe Thr Leu Thr Ile Ser Asp Leu
 65                  70                  75                  80

Glu Ser Asp Asp Ala Ala Thr Tyr Phe Cys Gln Gly Gly Tyr Arg Thr
                 85                  90                  95

Asp Ile Tyr Pro Phe Gly Gly Gly Thr Glu Val Val Val Lys
                100                 105                 110

<210> SEQ ID NO 7
<211> LENGTH: 116
<212> TYPE: PRT
<213> ORGANISM: Artificial Sequence
<220> FEATURE:
<223> OTHER INFORMATION: SEQ ID NO:7 (HC VR 4)

<400> SEQUENCE: 7

Gln Ser Val Glu Glu Ser Gly Gly Arg Leu Gly Thr Pro Gly Thr Pro
 1               5                  10                  15

Leu Thr Leu Thr Cys Thr Val Ser Gly Phe Ser Leu Ser Ser Tyr Val
                 20                  25                  30

Met Gly Trp Phe Arg Gln Ala Pro Gly Lys Gly Leu Glu Tyr Ile Gly
             35                  40                  45

Ile Ile Ser Ser Ser Gly Ser Pro Tyr Tyr Ala Ser Trp Val Asn Gly
 50                  55                  60

Arg Phe Thr Ile Ser Lys Thr Ser Thr Thr Met Asp Leu Lys Met Asn
 65                  70                  75                  80

Ser Pro Thr Thr Glu Asp Thr Ala Thr Tyr Phe Cys Ala Arg Val Gly
                 85                  90                  95

Pro Leu Gly Val Asp Tyr Phe Asn Ile Trp Gly Pro Gly Thr Leu Val
                100                 105                 110

Thr Val Ser Leu
            115

<210> SEQ ID NO 8
<211> LENGTH: 109
<212> TYPE: PRT
<213> ORGANISM: Artificial Sequence
<220> FEATURE:
<223> OTHER INFORMATION: SEQ ID NO:8 (LC VR 4)

<400> SEQUENCE: 8

Asp Ile Val Met Thr Gln Thr Pro Ser Ser Val Glu Ala Ala Val Gly
 1               5                  10                  15

Gly Thr Val Thr Ile Lys Cys Gln Ala Gly Gln Ser Ile Asn Ser Tyr
                 20                  25                  30

Leu Ala Trp Tyr Gln Gln Lys Pro Gly Gln Arg Pro Lys Leu Leu Ile
             35                  40                  45

Tyr Tyr Ala Ser Thr Leu Glu Ser Gly Val Pro Ser Arg Phe Lys Gly
 50                  55                  60

Ser Gly Ser Gly Thr Asp Tyr Thr Leu Thr Ile Ser Asp Leu Glu Ser
 65                  70                  75                  80

Ala Asp Ala Ala Thr Tyr Tyr Cys Gln Ser Trp His Tyr Ile Ser Arg
                 85                  90                  95

Ser Tyr Ala Phe Gly Gly Gly Thr Glu Val Val Val Lys
                100                 105

<210> SEQ ID NO 9
```

<211> LENGTH: 116
<212> TYPE: PRT
<213> ORGANISM: Artificial Sequence
<220> FEATURE:
<223> OTHER INFORMATION: SEQ ID NO:9 (HC VR 5)

<400> SEQUENCE: 9

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Val
            20                  25                  30
Met Gly Trp Phe Arg Gln Ala Ala Gly Lys Gly Leu Glu Tyr Ile Gly
        35                  40                  45
Tyr Ile Asn Ala Asp Gly Ser Pro Tyr Tyr Ala Thr Trp Val Asn Gly
    50                  55                  60
Arg Phe Thr Ile Ser Lys Thr Pro Thr Thr Met Asp Leu Lys Ile Asn
65                  70                  75                  80
Ser Pro Thr Thr Glu Asp Thr Ala Thr Tyr Phe Cys Ala Arg Val Gly
                85                  90                  95
Pro Leu Gly Val Asp Tyr Phe Asn Ile Trp Gly Pro Gly Thr Leu Val
            100                 105                 110
Thr Val Ser Leu
        115
```

<210> SEQ ID NO 10
<211> LENGTH: 109
<212> TYPE: PRT
<213> ORGANISM: Artificial Sequence
<220> FEATURE:
<223> OTHER INFORMATION: SEQ ID NO:10 (LC VR 5)

<400> SEQUENCE: 10

```
Asp Ile Val Met Thr Gln Thr Pro Ala Ser Val Glu Ala Ala Val Gly
1               5                   10                  15
Gly Thr Val Thr Ile Lys Cys Gln Ala Ser Gln Ser Ile Asn Arg Tyr
            20                  25                  30
Leu Thr Trp Tyr Gln Gln Lys Pro Gly Gln Arg Pro Lys Leu Leu Ile
        35                  40                  45
Tyr Tyr Ala Ser Thr Leu Glu Ser Gly Val Pro Ser Arg Phe Glu Gly
    50                  55                  60
Ser Gly Ser Gly Thr Asp Tyr Thr Leu Thr Ile Ser Asp Leu Glu Ser
65                  70                  75                  80
Ala Asp Ala Ala Thr Tyr Tyr Cys Gln Ser Tyr Tyr Ile Ser Arg
                85                  90                  95
Thr Tyr Ala Phe Gly Gly Gly Thr Glu Val Val Val Lys
            100                 105
```

<210> SEQ ID NO 11
<211> LENGTH: 116
<212> TYPE: PRT
<213> ORGANISM: Artificial Sequence
<220> FEATURE:
<223> OTHER INFORMATION: SEQ ID NO:11 (HC VR 6)

<400> SEQUENCE: 11

```
Gln Ser Val Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Tyr Thr
            20                  25                  30
```

```
Met Thr Trp Val Arg Gln Ala Pro Gly Lys Gly Leu Glu Trp Ile Gly
            35                  40                  45

Ile Ile Tyr Ala Gly Gly Ser Thr Ala Tyr Ala Ser Trp Ala Lys Gly
 50                  55                  60

Arg Phe Thr Ile Ser Lys Thr Ser Thr Val Asp Leu Lys Ile Thr
 65                  70                  75                  80

Ser Pro Thr Thr Glu Asp Thr Ala Thr Tyr Phe Cys Ala Arg Ser Ser
                 85                  90                  95

Ser Asp Gly Tyr Asp Tyr Phe Asn Ile Trp Gly Pro Gly Thr Leu Val
                100                 105                 110

Thr Val Ser Leu
        115
```

<210> SEQ ID NO 12
<211> LENGTH: 111
<212> TYPE: PRT
<213> ORGANISM: Artificial Sequence
<220> FEATURE:
<223> OTHER INFORMATION: SEQ ID NO:12 (LC VR 6)

<400> SEQUENCE: 12

```
Gly Val Val Met Thr Gln Thr Pro Ser Ser Val Ser Ala Ala Val Gly
 1               5                  10                  15

Gly Thr Val Thr Ile Asn Cys Gln Ala Ser Gln Ser Ile Gly Ser Trp
                20                  25                  30

Leu Ala Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Phe Ser Gly
 50                  55                  60

Arg Gly Ser Gly Thr His Phe Thr Leu Thr Ile Ser Asp Val Gln Ser
 65                  70                  75                  80

Asp Asp Ala Ala Thr Tyr Tyr Cys Gln Gln Thr Val Thr Ala Ala Ser
                 85                  90                  95

Asn Val Asp Asn Ala Phe Gly Gly Gly Thr Glu Val Val Val Lys
                100                 105                 110
```

<210> SEQ ID NO 13
<211> LENGTH: 115
<212> TYPE: PRT
<213> ORGANISM: Artificial Sequence
<220> FEATURE:
<223> OTHER INFORMATION: SEQ ID NO:13 (HC VR 7)

<400> SEQUENCE: 13

```
Arg Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser His Gly
                20                  25                  30

Ile Ser Trp Val Arg Gln Ala Pro Gly Lys Gly Leu Glu Tyr Ile Gly
            35                  40                  45

Thr Ile Gly Thr Gly Val Ile Thr Tyr Phe Ala Ser Trp Ala Lys Gly
 50                  55                  60

Arg Phe Thr Gly Ser Lys Thr Ser Thr Val Asp Leu Lys Ile Thr
 65                  70                  75                  80

Ser Pro Thr Thr Glu Asp Thr Ala Thr Tyr Phe Cys Ala Arg Gly Ser
                 85                  90                  95

Ala Trp Asn Asp Pro Phe Asp Pro Trp Gly Pro Gly Thr Leu Val Thr
                100                 105                 110
```

Val Ser Ser
        115

<210> SEQ ID NO 14
<211> LENGTH: 111
<212> TYPE: PRT
<213> ORGANISM: Artificial Sequence
<220> FEATURE:
<223> OTHER INFORMATION: SEQ ID NO:14 (LC VR 7)

<400> SEQUENCE: 14

Ala Leu Val Met Thr Gln Thr Pro Ala Ser Val Ser Ala Ala Val Gly
1               5                   10                  15

Gly Thr Val Thr Thr Lys Cys Gln Ala Ser Gln Ser Val Tyr Gly Asn
            20                  25                  30

Asn Asp Leu Ala Trp Tyr Gln His Lys Pro Gly Gln Pro Pro Lys Leu
        35                  40                  45

Leu Ile Tyr Leu Ala Ser Thr Leu Ala Thr Gly Val Pro Ser Arg Phe
    50                  55                  60

Ser Gly Ser Gly Ser Gly Thr Gln Phe Thr Leu Thr Ile Thr Gly Val
65                  70                  75                  80

Gln Ser Asp Asp Ala Ala Thr Tyr Tyr Cys Leu Gly Gly Gly Asp Asp
                85                  90                  95

Glu Ala Asp Asn Val Phe Gly Gly Gly Thr Glu Val Val Val Lys
            100                 105                 110

<210> SEQ ID NO 15
<211> LENGTH: 116
<212> TYPE: PRT
<213> ORGANISM: Artificial Sequence
<220> FEATURE:
<223> OTHER INFORMATION: SEQ ID NO:15 (HC VR 8)

<400> SEQUENCE: 15

Gln Ser Leu Glu Glu Ser Gly Gly Arg Leu Val Thr Pro Gly Thr Pro
1               5                   10                  15

Leu Thr Leu Thr Cys Thr Ala Ser Gly Val Asp Leu Ser Asn Tyr Ala
            20                  25                  30

Met Gly Trp Val Arg Gln Ala Pro Gly Lys Gly Leu Glu Trp Ile Gly
        35                  40                  45

Ile Ile Tyr Ala Gly Gly Ser Thr Ser Tyr Ala Thr Trp Ala Lys Gly
    50                  55                  60

Arg Phe Thr Ile Ser Lys Thr Ser Thr Thr Met Asp Leu Lys Met Thr
65                  70                  75                  80

Ser Pro Thr Thr Glu Asp Thr Ala Thr Tyr Phe Cys Ala Arg His Arg
                85                  90                  95

Ser Asp Gly Tyr Asp Tyr Phe His Leu Trp Gly Pro Gly Thr Leu Val
            100                 105                 110

Thr Val Ser Leu
        115

<210> SEQ ID NO 16
<211> LENGTH: 110
<212> TYPE: PRT
<213> ORGANISM: Artificial Sequence
<220> FEATURE:
<223> OTHER INFORMATION: SEQ ID NO:16 (LC VR 8)

<400> SEQUENCE: 16

```
Ala Ile Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Arg Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Val Gln Ser
65              70                  75                  80

Asp Asp Ala Ala Ala Tyr Tyr Cys Gln Gln Gly Tyr Ala Val Ser Tyr
            85                  90                  95

Val Glu Asn Ile Phe Gly Gly Gly Thr Glu Val Val Val Lys
            100                 105                 110
```

<210> SEQ ID NO 17
<211> LENGTH: 117
<212> TYPE: PRT
<213> ORGANISM: Artificial Sequence
<220> FEATURE:
<223> OTHER INFORMATION: SEQ ID NO:17 (HC VR 9)

<400> SEQUENCE: 17

```
Gln Ser Met Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Gly
            20                  25                  30

Val Ser Trp Val Arg Gln Ala Pro Gly Lys Gly Leu Glu Trp Ile Gly
        35                  40                  45

Ile Ile Tyr Gly Gly Ser Asp Ile Thr Ala Tyr Ala Ser Trp Ala Lys
    50                  55                  60

Gly Arg Phe Thr Ile Ser Lys Thr Ser Thr Thr Val Asp Leu Thr Ile
65              70                  75                  80

Thr Ser Pro Thr Thr Glu Asp Thr Ala Thr Tyr Phe Cys Ala Lys Ser
            85                  90                  95

Tyr Thr Asn Gly Met Asp Tyr Tyr Asn Ile Trp Gly Pro Gly Thr Leu
            100                 105                 110

Val Thr Val Ser Leu
            115
```

<210> SEQ ID NO 18
<211> LENGTH: 108
<212> TYPE: PRT
<213> ORGANISM: Artificial Sequence
<220> FEATURE:
<223> OTHER INFORMATION: SEQ ID NO:18 (LC VR 9)

<400> SEQUENCE: 18

```
Ala Phe Asp Leu Thr Gln Thr Pro Ser Ser Val Glu Ala Pro Val Gly
1               5                   10                  15

Gly Thr Val Ile Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Glu Thr Gln Phe Pro Leu Thr Ile Ser Asp Leu Glu Ser
65              70                  75                  80
```

Ala Asp Ala Ala Thr Tyr Tyr Cys Gln Ser Tyr Tyr Gly Ser Arg Ser
            85                  90                  95

Asn Val Phe Gly Gly Gly Thr Glu Val Val Val Lys
            100                 105

<210> SEQ ID NO 19
<211> LENGTH: 129
<212> TYPE: PRT
<213> ORGANISM: Artificial Sequence
<220> FEATURE:
<223> OTHER INFORMATION: SEQ ID NO:19 (HC VR 29AM4-5))

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Phe Ile His Trp Val Arg Gln Ala Pro Gly Lys Gly Leu Glu Trp Val
        35                  40                  45

Ala Ser Val Tyr Ser Ser Phe Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Thr Phe Pro Gly Leu Phe Asp Gly Phe Phe Gly Ala Tyr
            100                 105                 110

Leu Gly Ser Leu Asp Tyr Trp Gly Gln Gly Thr Leu Val Thr Val Ser
        115                 120                 125

Ser

<210> SEQ ID NO 20
<211> LENGTH: 110
<212> TYPE: PRT
<213> ORGANISM: Artificial Sequence
<220> FEATURE:
<223> OTHER INFORMATION: SEQ ID NO:20 (LC VR 29AM4-5)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Asn Trp Val Gly
                85                  90                  95

Ala Leu Val Thr Phe Gly Gln Gly Thr Lys Val Glu Ile Lys
            100                 105                 110

<210> SEQ ID NO 21
<211> LENGTH: 121
<212> TYPE: PRT
<213> ORGANISM: Artificial Sequence

```
<220> FEATURE:
<223> OTHER INFORMATION: SEQ ID NO:21 (HC VR 12C4)

<400> SEQUENCE: 21

Glu Val Lys Leu Glu Glu Ser Gly Gly Gly Leu Met Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Arg Asp Tyr Asp Tyr Ala Tyr Phe Asp Tyr Trp Gly
            100                 105                 110

Gln Gly Thr Thr Leu Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: SEQ ID NO:22 (LC VR 12C4)

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Tyr Thr Phe Gly Gly Thr Lys Leu Glu Ile Lys
            100                 105                 110

<210> SEQ ID NO 23
<211> LENGTH: 113
<212> TYPE: PRT
<213> ORGANISM: Artificial Sequence
<220> FEATURE:
<223> OTHER INFORMATION: SEQ ID NO:23 (HC KWAR23 )

<400> SEQUENCE: 23

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45
```

Gly Arg Ile Asp Pro Glu Asp Gly Glu Thr Lys Tyr Ala Pro Lys Phe
            50                  55                  60

Gln Asp Lys Ala Thr Ile Thr Ala Asp Thr Ser Ser Asn Thr Ala Tyr
 65                  70                  75                  80

Leu His Leu Ser Ser Leu Thr Ser Glu Asp Thr Ala Val Tyr Tyr Cys
                 85                  90                  95

Ala Arg Trp Gly Ala Tyr Trp Gly Gln Gly Thr Leu Val Thr Val Ser
            100                 105                 110

Ser

<210> SEQ ID NO 24
<211> LENGTH: 108
<212> TYPE: PRT
<213> ORGANISM: Artificial Sequence
<220> FEATURE:
<223> OTHER INFORMATION: SEQ ID NO:24 (LC VR KWAR23)

<400> SEQUENCE: 24

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Ser Ser Ser
             20                  25                  30

Tyr Leu Tyr Trp Tyr Gln Gln Lys Pro Gly Ser Ser Pro Lys Leu Trp
         35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                 85                  90                  95

Arg Thr Phe Gly Ala Gly Thr Lys Leu Glu Leu Lys
            100                 105

<210> SEQ ID NO 25
<211> LENGTH: 330
<212> TYPE: PRT
<213> ORGANISM: Artificial Sequence
<220> FEATURE:
<223> OTHER INFORMATION: SEQ ID NO 25: (human IgG1 antibody HC constant
      region)

<400> SEQUENCE: 25

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 107
<212> TYPE: PRT
<213> ORGANISM: Artificial Sequence
<220> FEATURE:
<223> OTHER INFORMATION: SEQ ID NO 26: (human IgG antibody LC  constant
      region)

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 330
<212> TYPE: PRT
<213> ORGANISM: Artificial Sequence
<220> FEATURE:
<223> OTHER INFORMATION: SEQ ID NO 27: (human IgG1 antibody HC constant region LALA mutant (mutations underlined)

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 19
<212> TYPE: PRT
<213> ORGANISM: Artificial Sequence
<220> FEATURE:
<223> OTHER INFORMATION: SEQ ID NO:28 (leader sequence antibodies 1-9)

<400> SEQUENCE: 28

Met Gly Trp Ser Cys Ile Ile Leu Phe Leu Val Ala Thr Ala Thr Gly
1               5                   10                  15

Val His Ser

<210> SEQ ID NO 29
<211> LENGTH: 21
<212> TYPE: PRT
<213> ORGANISM: Artificial Sequence
<220> FEATURE:
<223> OTHER INFORMATION: SEQ ID NO:29 (HAVT20 leader sequence)

<400> SEQUENCE: 29

Met Ala Cys Pro Gly Phe Leu Trp Ala Leu Val Ile Ser Thr Cys Leu
1               5                   10                  15

Glu Phe Ser Met Ala
            20

<210> SEQ ID NO 30
<211> LENGTH: 117
<212> TYPE: PRT
<213> ORGANISM: Artificial Sequence
<220> FEATURE:
<223> OTHER INFORMATION: SEQ ID NO:30 (HC10

<400> SEQUENCE: 30

Lys Val Glu Glu Ser Gly Gly Gly Leu Val Gln Pro Gly Gly Ser Leu
1               5                   10                  15

Arg Leu Ser Cys Ala Ala Ser Gly Phe Ser Leu Ser Ser Tyr Val Met
            20                  25                  30

Gly Trp Val Arg Gln Ala Pro Gly Lys Gly Leu Glu Trp Val Ser Ile
        35                  40                  45

Ile Ser Ser Ser Gly Ser Pro Tyr Tyr Ala Ser Trp Val Asn Gly Arg
    50                  55                  60

Phe Thr Ile Ser Lys Asp Asn Ser Glu Gly Met Val Tyr Leu Gln Met
65                  70                  75                  80

Asn Ser Leu Arg Ala Glu Asp Thr Ala Val Tyr Tyr Cys Ala Arg Val
                85                  90                  95

Gly Pro Leu Gly Val Asp Tyr Phe Asn Ile Trp Gly Gln Gly Thr Thr
            100                 105                 110

Val Thr Val Ser Ser
        115

<210> SEQ ID NO 31
<211> LENGTH: 109
<212> TYPE: PRT
<213> ORGANISM: Artificial Sequence
<220> FEATURE:
<223> OTHER INFORMATION: SEQ ID NO:31 (LC 10)

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Gln Ala Gly Gln Ser Ile Asn Ser Tyr
            20                  25                  30

Leu Ala Trp Tyr Gln Gln Lys Pro Gly Gln Pro Pro Lys Leu Leu Ile
        35                  40                  45

Tyr Tyr Ala Ser Thr Leu Glu Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Ser Trp His Tyr Ile Ser Arg

```
                    85                  90                  95

Ser Tyr Ala Phe Gly Gly Gly Thr Lys Leu Glu Ile Lys
                100                 105

<210> SEQ ID NO 32
<211> LENGTH: 117
<212> TYPE: PRT
<213> ORGANISM: Artificial Sequence
<220> FEATURE:
<223> OTHER INFORMATION: SEQ ID NO:32 (HC VR 11)

<400> SEQUENCE: 32

Glu Val Lys Val Glu Glu Ser Gly Gly Leu Val Gln Pro Gly Gly
1               5                   10                  15

Ser Leu Arg Leu Ser Cys Ala Ala Ser Gly Phe Ser Leu Ser Ser Tyr
                20                  25                  30

Val Met Gly Trp Val Arg Gln Ala Pro Gly Lys Gly Leu Glu Trp Val
            35                  40                  45

Ser Ile Ile Ser Ser Ser Gly Ser Pro Tyr Tyr Ala Ser Trp Val Asn
        50                  55                  60

Gly Arg Phe Thr Ile Ser Lys Thr Ser Thr Thr Met Asp Leu Gln Met
65                  70                  75                  80

Asn Ser Leu Arg Ala Glu Asp Thr Ala Val Tyr Tyr Cys Ala Arg Val
                85                  90                  95

Gly Pro Leu Gly Val Asp Tyr Phe Asn Ile Trp Gly Gln Gly Thr Thr
                100                 105                 110

Val Thr Val Ser Ser
        115

<210> SEQ ID NO 33
<211> LENGTH: 109
<212> TYPE: PRT
<213> ORGANISM: Artificial Sequence
<220> FEATURE:
<223> OTHER INFORMATION: SEQ ID NO:33 (LC VR 11)

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Ser Ile Asn Ser Tyr
                20                  25                  30

Leu Ala Trp Tyr Gln Gln Lys Pro Gly Lys Val Pro Lys Leu Leu Ile
            35                  40                  45

Tyr Tyr Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Trp His Tyr Ile Ser Arg
                85                  90                  95

Ser Tyr Ala Phe Gly Gln Gly Thr Lys Val Glu Ile Lys
                100                 105

<210> SEQ ID NO 34
<211> LENGTH: 116
<212> TYPE: PRT
<213> ORGANISM: Artificial Sequence
<220> FEATURE:
<223> OTHER INFORMATION: SEQ ID NO:34 (HC VR 12)

<400> SEQUENCE: 34
```

Val Gln Leu Val Glu Ser Gly Gly Arg Leu Val Gln Pro Gly Thr Pro
1               5                   10                  15

Leu Thr Leu Ser Cys Thr Val Ser Gly Phe Ser Leu Ser Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
    50                  55                  60

Arg Phe Thr Ile Ser Lys Thr Ser Thr Thr Met Asp Leu Lys Met Asn
65                  70                  75                  80

Ser Leu Arg Ser Glu Asp Thr Ala Thr Tyr Phe Cys Ala Arg Val Gly
            85                  90                  95

Pro Leu Gly Val Asp Tyr Phe Asn Ile Trp Gly Pro Gly Thr Leu Val
            100                 105                 110

Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: SEQ ID NO:34 (HC VR 12)

<400> SEQUENCE: 35

Val Gln Leu Val Glu Ser Gly Gly Arg Leu Val Gln Pro Gly Thr Pro
1               5                   10                  15

Leu Thr Leu Ser Cys Thr Val Ser Gly Phe Ser Leu Ser Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
    50                  55                  60

Arg Phe Thr Ile Ser Lys Thr Ser Thr Thr Met Asp Leu Lys Met Asn
65                  70                  75                  80

Ser Leu Arg Ser Glu Asp Thr Ala Thr Tyr Phe Cys Ala Arg Val Gly
            85                  90                  95

Pro Leu Gly Val Asp Tyr Phe Asn Ile Trp Gly Pro Gly Thr Leu Val
            100                 105                 110

Thr Val Ser Ser
        115

<210> SEQ ID NO 36
<211> LENGTH: 111
<212> TYPE: PRT
<213> ORGANISM: Artificial Sequence
<220> FEATURE:
<223> OTHER INFORMATION: SEQ ID NO:36 (LC VR 13)

<400> SEQUENCE: 36

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Gly Asn
            20                  25                  30

Asn Asp Leu Ala Trp Tyr Gln Gln Lys Pro Gly Lys Ala Pro Lys Leu
        35                  40                  45

Leu Ile Tyr Leu Ala Ser Thr Leu Ala Thr Gly Val Pro Ser Arg Phe

```
                50                  55                  60
Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Leu Gly Gly Gly Asp Asp
                 85                  90                  95

Glu Ala Asp Asn Val Phe Gly Gly Gly Thr Lys Val Glu Ile Lys
                100                 105                 110

<210> SEQ ID NO 37
<211> LENGTH: 111
<212> TYPE: PRT
<213> ORGANISM: Artificial Sequence
<220> FEATURE:
<223> OTHER INFORMATION: SEQ ID NO:37 (LC VR 14 +16)

<400> SEQUENCE: 37

Asp Ile Glu Met Thr Gln Ser Pro Ser Ser Val Ser Ala Ser Val Gly
  1               5                  10                  15

Asp Arg Val Thr Leu Thr Cys Gln Ala Ser Gln Ser Val Tyr Gly Asn
                 20                  25                  30

Asn Asp Leu Ala Trp Tyr Gln Gln Lys Pro Gly Gln Ala Pro Lys Leu
             35                  40                  45

Leu Ile Tyr Leu Ala Ser Thr Leu Ala Thr Gly Val Pro Ser Arg Phe
         50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Leu Gly Gly Gly Asp Asp
                 85                  90                  95

Glu Ala Asp Asn Val Phe Gly Gly Gly Thr Lys Val Glu Ile Lys
                100                 105                 110

<210> SEQ ID NO 38
<211> LENGTH: 111
<212> TYPE: PRT
<213> ORGANISM: Artificial Sequence
<220> FEATURE:
<223> OTHER INFORMATION: SEQ ID NO:38 (LC VR 15)

<400> SEQUENCE: 38

Glu Leu Val Met Thr Gln Ser Pro Ser Ser Leu Ser Ala Ser Val Gly
  1               5                  10                  15

Asp Arg Val Thr Ile Thr Cys Gln Ala Ser Gln Ser Val Tyr Gly Asn
                 20                  25                  30

Asn Asp Leu Ala Trp Tyr Gln Gln Lys Pro Gly Glu Ala Pro Lys Leu
             35                  40                  45

Leu Ile Tyr Leu Ala Ser Thr Leu Ala Thr Gly Val Pro Ser Arg Phe
         50                  55                  60

Ser Gly Ser Gly Ser Gly Thr Asp Phe Thr Leu Thr Ile Ser Gly Leu
 65                  70                  75                  80

Gln Ser Glu Asp Phe Ala Thr Tyr Tyr Cys Leu Gly Gly Gly Asp Asp
                 85                  90                  95

Glu Ala Asp Asn Val Phe Gly Gln Gly Thr Lys Val Glu Ile Lys
                100                 105                 110

<210> SEQ ID NO 39
<211> LENGTH: 19
<212> TYPE: PRT
<213> ORGANISM: Artificial Sequence
<220> FEATURE:
```

```
<223> OTHER INFORMATION: SEQ ID NO:39 (leader sequence heavy chains
      10-14)

<400> SEQUENCE: 39

Met Gly Trp Thr Leu Val Phe Leu Phe Leu Leu Ser Val Thr Ala Gly
1               5                   10                  15

Val His Ser

<210> SEQ ID NO 40
<211> LENGTH: 20
<212> TYPE: PRT
<213> ORGANISM: Artificial Sequence
<220> FEATURE:
<223> OTHER INFORMATION: SEQ ID NO:40 (leader sequence light chains 10,
      11, 13-16)

<400> SEQUENCE: 40

Met Val Ser Ser Ala Gln Phe Leu Gly Leu Leu Leu Leu Cys Phe Gln
1               5                   10                  15

Gly Thr Arg Cys
            20
```